(12) United States Patent
Liu et al.

(10) Patent No.: US 8,188,272 B2
(45) Date of Patent: May 29, 2012

(54) FUSED HETEROCYCLIC COMPOUNDS USEFUL AS KINASE MODULATORS

(75) Inventors: Chunjian Liu, Pennington, NJ (US); Katerina Leftheris, Skillman, NJ (US); Andrew J. Tebben, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 280 days.

(21) Appl. No.: 12/532,330

(22) PCT Filed: Mar. 20, 2008

(86) PCT No.: PCT/US2008/057656
§ 371 (c)(1), (2), (4) Date: Dec. 2, 2009

(87) PCT Pub. No.: WO2008/116064
PCT Pub. Date: Sep. 25, 2008

(65) Prior Publication Data
US 2010/0105676 A1   Apr. 29, 2010

Related U.S. Application Data

(60) Provisional application No. 60/776,003, filed on Mar. 21, 2007.

(51) Int. Cl.
C07D 487/04 (2006.01)
C07D 401/04 (2006.01)
A61K 31/4188 (2006.01)
A61K 31/53 (2006.01)
A61P 19/02 (2006.01)

(52) U.S. Cl. .................................. 544/184; 514/243

(58) Field of Classification Search .................. 544/184; 514/243
See application file for complete search history.

(56) References Cited

U.S. PATENT DOCUMENTS

| 4,200,750 | A | 4/1980 | Warner, Jr. et al. |
| 7,470,693 | B2 | 12/2008 | Borzilleri et al. |
| 7,547,782 | B2 | 6/2009 | Borzilleri et al. |
| 2006/0084650 | A1 | 4/2006 | Dong et al. |
| 2007/0078136 | A1* | 4/2007 | Vaccaro et al. ............. 514/243 |
| 2008/0045536 | A1 | 2/2008 | Vaccaro et al. |

FOREIGN PATENT DOCUMENTS

| WO | WO 2004/021989 | 3/2004 |
| WO | WO 2004/046331 | 6/2004 |
| WO | WO 2005/005429 | 1/2005 |
| WO | WO 2005/014599 | 2/2005 |
| WO | WO 2005/047290 | 5/2005 |
| WO | WO 2006/004636 | 1/2006 |
| WO | WO 2006/053121 | 5/2006 |
| WO | WO 2006/065755 | 6/2006 |
| WO | WO 2006/065788 | 6/2006 |
| WO | WO 2006/099075 | 9/2006 |
| WO | WO 2007/025043 | 3/2007 |
| WO | WO 2007/038314 | 4/2007 |
| WO | WO 2008/003511 | 1/2008 |

OTHER PUBLICATIONS

Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661, 2000.*
Chou and Talalay, *Adv. Enzyme Regul.* 1984, 22:27-55.

* cited by examiner

*Primary Examiner* — Venkataraman Balasubramanian
(74) *Attorney, Agent, or Firm* — Laurelee A. Duncan; Hong Liu

(57) ABSTRACT

Compounds having the formula (I), and enantiomers, and diastereomers, pharmaceutically-acceptable salts, thereof, [PLEASE INSERT CHEMICAL STRUCTURE HERE] (I) are useful as kinase modulators, including Btk modulation, wherein R1, R2, R4, Q, Y, A and D are as defined herein.

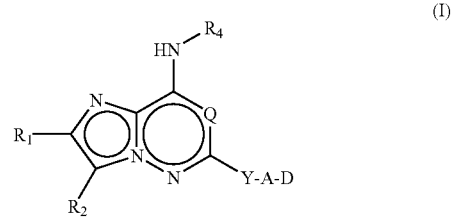

11 Claims, No Drawings

US 8,188,272 B2

FUSED HETEROCYCLIC COMPOUNDS USEFUL AS KINASE MODULATORS

This application claims the benefit of priority to U.S. Ser. No. 60/776,003, filed Mar. 21, 2007.

FIELD OF THE INVENTION

This invention relates to fused heterocyclic compounds useful as kinase modulators, including the modulation of Btk. Provided herein are certain imidazotriazines and related compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk, in a mammal.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development, as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics (such as Ritaxan) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds that modulate protein kinases such as Btk and methods of using these compounds should provide substantial therapeutic benefits to a wide variety of patients.

Inhibitors of protein kinases are widely sought and a number of publications report effective classes of compounds. For example, patent publications WO 2005/047290, WO 2005/014599, WO 2005/005429, WO 2006/099075, and WO 2006/053121 disclose certain imidazopyrazine compounds that are said to inhibit protein kinase activity, including Btk activity. In U.S. Publication No. 2006/0084650, it is disclosed that fused heterocyclic compounds exemplified by imidazopyrimidines and pyrrolotriazines may be used as protein kinase inhibitors. In addition, certain imidazopyridazine and imidazotriazine compounds are disclosed in WO 2007/038314 (published Apr. 5, 2007) and WO 2008/0045536 (published Feb. 21, 2008), both of which are assigned to the present assignee.

The present invention relates to a new class of substituted imidazotriazines found to be effective inhibitors of protein kinases, particularly Btk. These novel compounds are provided to be useful as pharmaceuticals with desirable stability, bioavailability, therapeutic index and toxicity values that are important to their drugability.

SUMMARY OF THE INVENTION

Modulators of kinase activity which may generally be described as imidazotriazines and related compounds are provided herein.

Provided is at least one chemical entity chosen from compounds of the formula (I):

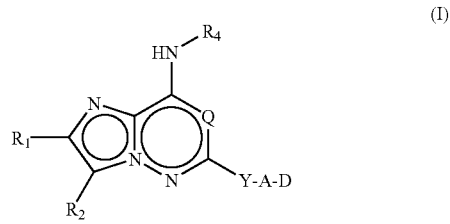

or an enantiomer, diastereomer, or a pharmaceutically-acceptable salt thereof, wherein
Q is N;
Y is NR$_6$R$_7$, wherein R$_6$ and R$_7$ are taken together with the nitrogen atom to which they are both attached to form an optionally substituted heterocyclo or optionally substituted heteroaryl;

A is selected from NH, NH$_2$, NHCO, NHCON, NHCONH, NHCONH$_2$ and NH$_2$COO;

D is optionally substituted alkyl, optionally substituted alkoxy, optionally substituted cycloalkyl, optionally substituted aryl, optionally substituted heterocyclo, optionally substituted heteroaryl or is absent;

R$_1$ is selected from hydrogen, optionally substituted C$_{1-4}$ alkyl, and cyano;

R$_2$ is selected from hydrogen, optionally substituted C$_{1-4}$ alkyl, amino, cyano, halogen, optionally substituted amide, and optionally substituted carboxamide; and R$_4$ is selected from hydrogen, optionally substituted aryl, optionally substituted heterocyclo and optionally substituted heteroaryl.

The present invention further provides at least one chemical entity chosen from compounds of the formula (II):

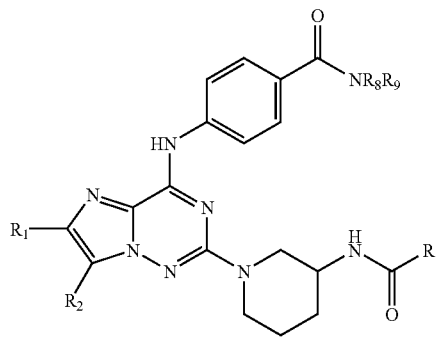

(II)

or an enantiomer, diastereomer, or a pharmaceutically-acceptable salt thereof, wherein R$_1$ is hydrogen;

R$_2$ is selected from hydrogen, amino, cyano, optionally substituted C$_{1-4}$ alkyl, —C(=O)NR$_{11}$R$_{12}$, and —NR$_{11}$C(=O)R$_{12}$, wherein R$_{11}$ and R$_{12}$ are each independently selected from hydrogen, C$_{1-4}$alkyl, C$_{3-7}$cycloalkyl, aryl, heteroaryl, and heterocyclo;

R$_8$ and R$_9$ are each independently selected from hydrogen, optionally substituted alkyl, optionally substituted alkoxy, optionally substituted cycloalkyl, and optionally substituted heterocyclo or heteroaryl; or R$_8$ and R$_9$ may be taken together with the nitrogen atom to which they are both attached to form an optionally substituted heterocyclo or optionally substituted heteroaryl; and R$_{10}$ is selected from optionally substituted alkyl, optionally substituted alkoxy, optionally substituted cycloalkyl, optionally substituted aryl, optionally substituted heterocyclo and optionally substituted heteroaryl.

The present invention is also directed to pharmaceutical compositions useful in treating diseases associated with kinase modulation, including modulation (especially inhibition) of Btk, comprising compounds of formula (I) or (II), or pharmaceutically-acceptable salts thereof, and pharmaceutically-acceptable carriers or diluents. The invention further relates to methods of treating diseases associated with the kinase modulation, including the modulation of Btk, comprising administering to a patient in need of such treatment a therapeutically-effective amount of a compound according to formula (I) or (II).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "C$_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy(C$_{0-2}$)alkyl or (C$_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$ —SO$_2$NR$_a$R$_b$, —SO$_2$NR$_a$C(=O) R$_b$, SO$_3$H, —OC(O)R$_a$, —C(=O)R$_a$, —CO$_2$R$_a$, —C(=O) NR$_a$R$_b$, —C(=O)(C$_{1-4}$alkylene)NR$_a$R$_b$, —C(=O)NR$_a$ (SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$ and R$_b$ are selected from hydrogen, alkyl, alkenyl, CO$_2$H, CO$_2$(alkyl), C$_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and R$_c$ is selected from same groups as R$_a$ and R$_b$ but is not hydrogen. Each group R$_a$ and R$_b$ when other than hydrogen, and each R$_c$ group optionally has up to three further substituents attached at any available carbon or nitrogen atom of R$_a$, R$_b$, and/or R$_c$, said substituent(s) being selected from the group consisting of (C$_{1-6}$)alkyl, (C$_{2-6}$)alkenyl, hydroxy, halogen, cyano, nitro, =O (as valence allows), CF$_3$, O(C$_{1-6}$alkyl), OCF$_3$, C(=O)H, C(=O)(C$_{1-6}$alkyl), CO$_2$H, CO$_2$(C$_{1-6}$alkyl), NHCO$_2$(C$_{1-6}$ alkyl), —S(C$_{1-6}$alkyl), —NH$_2$, NH(C$_{1-6}$alkyl), N(C$_{1-6}$ alkyl)$_2$, N(CH$_3$)$_3^+$, SO$_2$(C$_{1-6}$alkyl), C(=O)(C$_{1-4}$alkylene) NH$_2$, C(=O)(C$_{1-4}$alkylene)NH(alkyl), C(=O)(C$_{1-4}$alkylene)N(C$_{1-4}$alkyl)$_2$, C$_{3-7}$cycloalkyl, phenyl, benzyl, phenylethyl, phenyloxy, benzyloxy, napthyl, a four to seven membered heterocyclo or cycloalkyl, or a five to six membered heteroaryl. When a substituted alkyl is substituted with an aryl (including, for example, phenyl and napthyl), heterocyclo, cycloalkyl, or heteroaryl group, said ringed systems are as defined below and thus may have zero, one, two, or three substituents, also as defined below.

One skilled in the field will understand that, when the designation "CO$_2$" is used herein, this is intended to refer to the group

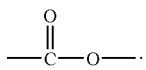

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl (C$_{0-4}$)alkyl includes a substituted lower alkyl having at least one aryl substituent and also includes an aryl directly bonded to another group, i.e., aryl(C$_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in C$_{2-3}$heteroalkylene, the subscript refers to the number of carbon atoms in the group in addition to heteroatoms. Thus, for example, a C$_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteroalkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—C$_{1-6}$alkyl.

The term "alkylthio" refers to a sulfur atom that is substituted by an alkyl or substituted alkyl group as defined herein. For example, the term "thioalkyl" includes the group —S—C$_{1-6}$alkyl, and so forth.

The term "alkylamino" refers to an amino group substituted with an alkyl group or substituted alkyl group as defined above. For example, the term "alkylamino" includes the group —NR—C$_{1-12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent C$_{1-2}$-aminoalkyl includes the groups —CH$_2$—N(CH$_3$)$_2$, and —(CH$_2$)$_2$—NH$_2$. A lower aminoalkyl comprises an aminoalkyl having one to four carbon atoms. The term (C$_{1-4}$alkyl)$_{0-2}$amino includes the groups NH$_2$, —NH(C$_{1-4}$alkyl), and —N(C$_{1-4}$alkyl)$_2$. "Amino" refers to the group NH$_2$. A "substituted amino" refers to an amino group substituted as described above for the nitrogen atom of a heteroalkylene chain and includes, for example, the terms alkylamino and acylamino (—NR$_d$C(O)R$_e$).

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, whereas a bivalent alkoxy includes groups such as —O—C$_{1-12}$alkylene-.

It should be understood that the selections for all groups, including for example, alkoxy, thioalkyl, and aminoalkyl, will be made by one skilled in the field to provide stable compounds.

The term "carbonyl" refers to a bivalent carbonyl group —C(=O). When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is a heterocyclo, such as morpholinyl.

The term "acyl" refers to a carbonyl group linked to an organic radical, more particularly, the group C(=O)R$_e$. The group R$_e$ can be selected from alkyl, alkenyl, alkynyl, aminoalkyl, substituted alkyl (i.e., substituted alkylene), substituted alkenyl, substituted alkynyl, cycloalkyl, heterocyclo, aryl, or heteroaryl, as defined herein. When R$_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

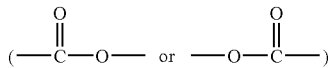

linked to an organic radical (CO$_2$R$_e$), as well as the bivalent groups —CO$_2$—, —CO$_2$R$_e$— which are linked to organic radicals in compounds of formula (I), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.)

The term "carboxamide", "carboxamidyl", or "carboxamido" refers to the group —NR$_d$C(=O)R$_e$, wherein the groups R$_d$ and R$_e$ are defined as recited above in the definitions for heteroalkyl, alkoxycarbonyl and acyl. For example, the group

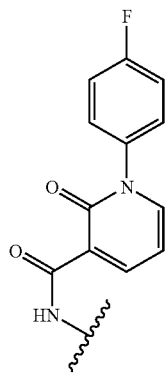

is a carboxamido group where R$_e$ is a substituted heterocyclo according to the definitions herein.

The term "amide", "amidyl", or "amido" refers to the group —C(=O)NR$_a$R$_b$, wherein the groups R$_a$ and R$_b$ are defined as recited above in the definition for substituted alkyl groups.

The term "urea" refers to the group —NR$_d$C(=O)NR$_a$R$_b$, wherein the groups R$_a$, R$_b$, and R$_d$ are defined as recited above in the definition for substituted alkyl groups. Additionally, the urea group may be bivalent, in which case one of the groups R$_a$ and R$_b$ will be a bond.

The term "sulfonyl" refers to a sulphoxide group linked to an organic radical, more particularly, the monovalent group —S(O)$_2$—R$_e$. Additionally, the sulfonyl group may be bivalent, in which case R$_e$ is a bond. The group R$_e$ is selected from those recited above for acyl and alkoxycarbonyl groups, with the exception that R$_e$ is not hydrogen.

The terms "sulfonamide", "sulfonamidyl", or "sulfonamido" refers to the group —S(O)$_2$NR$_a$R$_b$, wherein R$_a$ and R$_b$ are as defined above for substituted alkyl groups.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

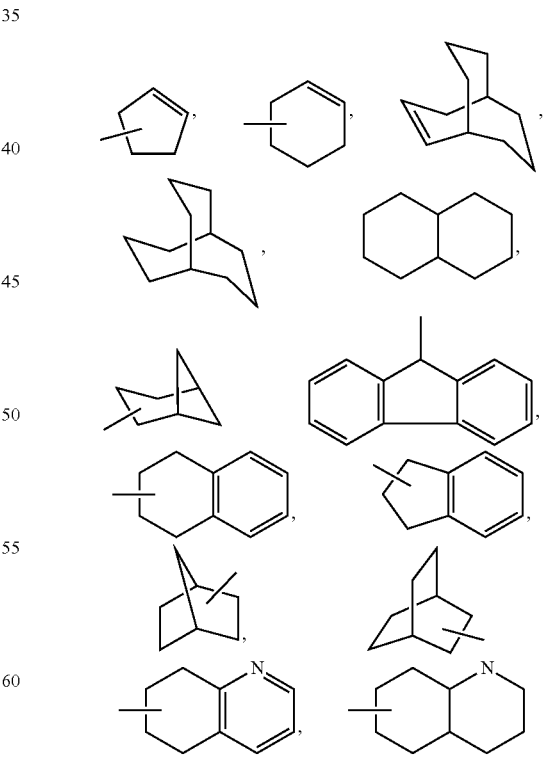

and the like, which optionally may be substituted at any available atoms of the ring(s). Preferred cycloalkyl groups include cyclopropyl, cyclopentyl, cyclohexyl, and

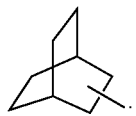

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), SO$_3$H, —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —C(=O)R$_a$, —CO$_2$R$_a$, —C(=O)NR$_a$R$_b$, —C(=O)(C$_{1-4}$ alkylene)NR$_a$R$_b$, —C(=O)NR$_a$(SO$_2$)R$_b$, —CO$_2$(C$_{1-4}$ alkylene)NR$_a$R$_b$, —NR$_a$C(=O)R$_b$, —NR$_a$CO$_2$R$_b$, —NR$_a$(C$_{1-4}$ alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$ alkyl), —S(C$_{1-4}$alkyl), —NH$_2$, NH(C$_{1-4}$alkyl), N(C$_{1-4}$ alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$ alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Thus, examples of aryl groups include:

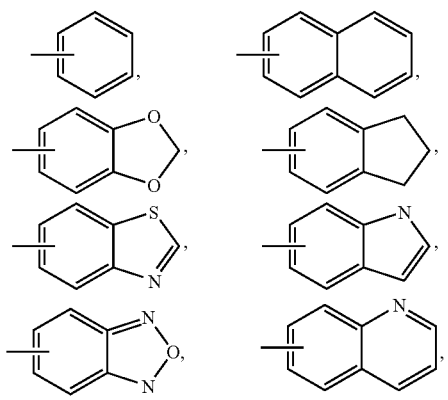

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —C(=O)R$_a$, —CO$_2$R$_a$, —C(=O)NR$_a$R$_b$, —C(=O)(C$_{1-4}$ alkylene)NR$_a$R$_b$, —C(=O)NR$_a$(SO$_2$)R$_b$, —CO$_2$(C$_{1-4}$alkylene)NR$_a$R$_b$, —NR$_a$CO$_2$R$_b$, —NR$_a$(C$_{1-4}$ alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above. When a heterocyclo is substituted with a further ring, said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$ (C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl

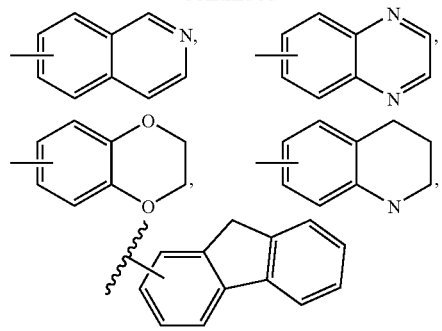

sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

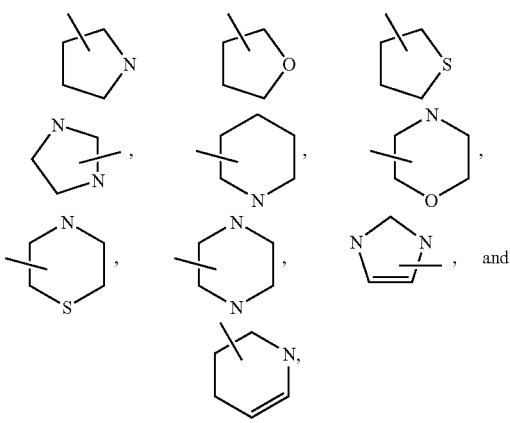

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)$ $R_b$, $SO_3H$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$alkyl, ($C_{2-4}$) alkenyl, ($C_{2-4}$)alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH$ (alkyl), $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

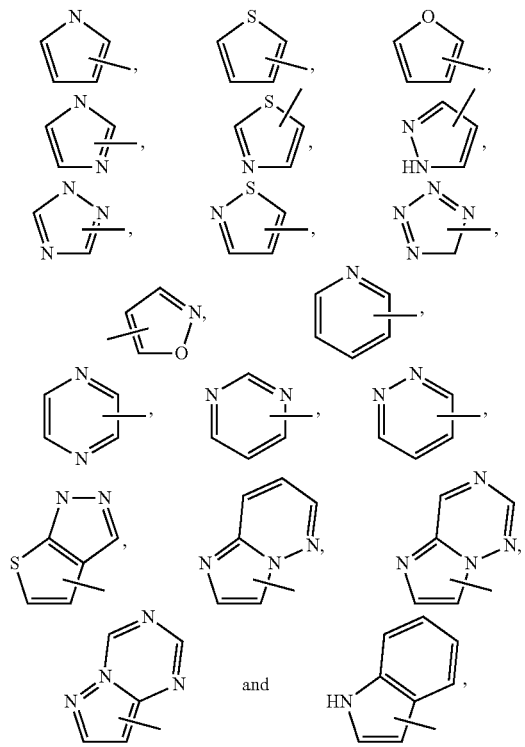

and the like, which optionally may be substituted at any available carbon or nitrogen atom. Aromatic rings may also be designated by an unbroken circle in the ring. For example the core ring of formula (I),

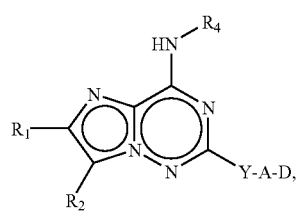

represents a bicyclic heteroaryl group.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

Generally, for a non-formula substituent listing a combination of groups, unless specifically designated otherwise, the last group of the combination is the point of attachment with adjacent groups attached sequentially. Accordingly, for example, the term "aminocyclohexylmethyl is intended" to mean

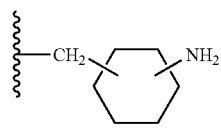

and N-(n-propyl)sulfonamido is intended to mean

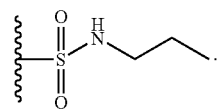

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) or (II) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) or (II) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt.

However, other salts may be useful, e.g., in isolation or purification steps which may be employed during preparation, and thus, are contemplated within the scope of the invention. Salts of the compounds of the formula (I) or (II) may be formed, for example, by reacting a compound of the formula (I) or (II) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the inventive compounds are also contemplated. The term "prodrug" denotes a compound which, upon administration to a subject, undergoes chemical conversion by metabolic or chemical processes to yield a compound of the formula (I) or (II), and/or a salt and/or solvate thereof. Any compound that will be converted in vivo to provide the bioactive agent (i.e., the compound for formula (I) or (II)) is a prodrug within the scope and spirit of the invention. For example, compounds containing a carboxy group can form physiologically hydrolyzable esters which serve as prodrugs by being hydrolyzed in the body to yield formula (I) or (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) or (II) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) or (II) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

It should further be understood that solvates (e.g., hydrates) of the compounds of Formula (I) or (II) are also with the scope of the present invention. Methods of solvation are generally known in the art.

Preferred Compounds

Preferred compounds are those within the scope of formula (I),

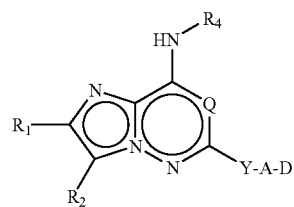

their enantiomers, diastereomers, pharmaceutically-acceptable salts, or hydrates thereof. In formula (I), $R_1$, $R_2$, $R_4$, Q, Y, A and D are as defined herein. Moreover, Y is preferably selected from:

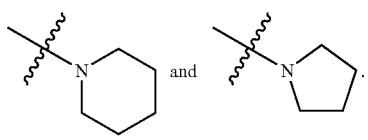

Other preferred compounds, including enantiomers, diastereomers, pharmaceutically-acceptable salts, or hydrates thereof, are those within the scope of formula (II):

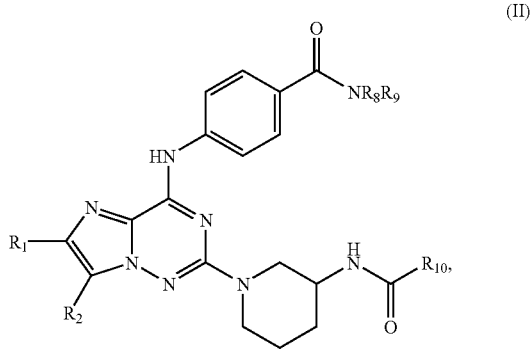

in which, $R_1$ is hydrogen;

$R_2$ is selected from hydrogen, amino, cyano, optionally substituted $C_{1-4}$ alkyl, —C(=O)NR$_{11}$R$_{12}$, and —NR$_{11}$C(=O)R$_{12}$, wherein $R_{11}$ and $R_{12}$ are each independently selected from hydrogen, $C_{1-4}$alkyl, $C_{3-7}$cycloalkyl, aryl, heteroaryl, and heterocyclo;

$R_8$ and $R_9$ are each independently selected from hydrogen, optionally substituted alkyl, optionally substituted alkoxy, optionally substituted cycloalkyl, and optionally substituted heterocyclo or heteroaryl; or $R_8$ and $R_9$ may be taken together with the nitrogen atom to which they are both attached to form an optionally substituted heterocyclo or optionally substituted heteroaryl; and $R_{10}$ is selected from optionally substituted alkyl, optionally substituted alkoxy, optionally substituted cycloalkyl, optionally substituted aryl, optionally substituted heterocyclo and optionally substituted heteroaryl.

More preferred compounds, including enantiomers, diastereomers, pharmaceutically-acceptable salts, or hydrates thereof, within the scope of formula (II) are those in which $R_8$ and $R_9$ are each independently selected from hydrogen, $C_{1-4}$alkyl, heteroaryl, and heterocyclo, wherein said $C_{1-4}$alkyl, heteroaryl, and heterocyclo are optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —NR$_{13}$R$_{14}$, and —C(O)OR$_{13}$ wherein $R_{13}$ and $R_{14}$ are each independently selected from hydrogen, $C_{1-4}$alkyl, and heterocyclo. More preferably —NR$_8$R$_9$ is selected from:

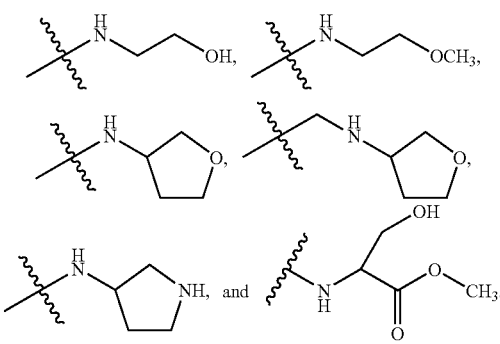

Other more preferred compounds, including enantiomers, diastereomers, pharmaceutically-acceptable salts, or hydrates thereof, within the scope of formula (II) are those in which $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, wherein said heteroaryl and heterocyclo are independently optionally substituted as valence allows with one or more substituents selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —O($C_{1-4}$alkyl), —C(=O)H, —C(=O), —S($C_{1-4}$alkyl), —NH$_2$, —NH($C_{1-4}$alkyl), —N($C_{1-4}$alkyl)$_2$, —NH(alkylene)OR$_{17}$ wherein $R_{17}$ is selected from hydrogen and $C_{1-4}$alkyl.

More preferably, $R_8$ and $R_9$ are taken together with the nitrogen atom to which they are both attached to form the following substituents:

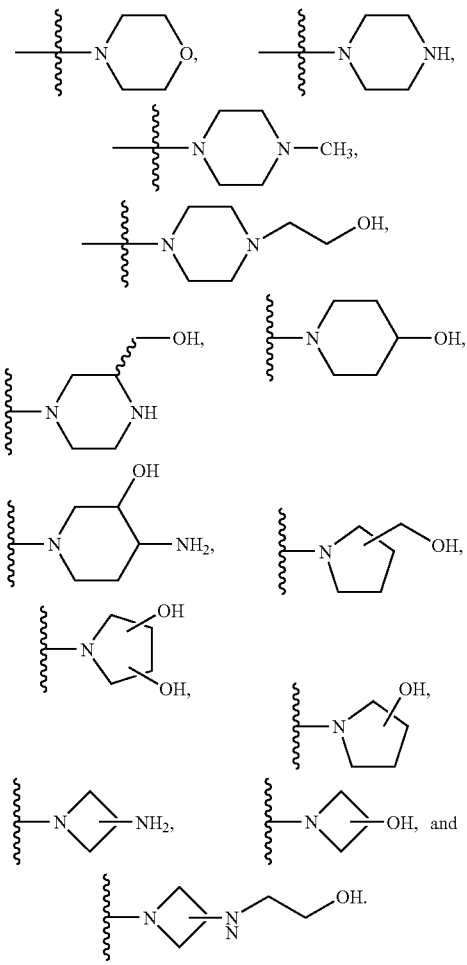

Other more preferred compounds, including enantiomers, diastereomers, pharmaceutically-acceptable salts, or hydrates thereof, within the scope of formula (II) are those in which $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —OR$_{15}$, —NR$_{15}$R$_{16}$, —NR$_{15}$C(=O)R$_{16}$, —CO$_2$R$_{15}$, —C(=O)R$_{15}$, —C(=O)R$_{15}$, —C(=O)NR$_{15}$R$_{16}$, cycloalkyl, heterocyclo, aryl, and heteroaryl wherein said cycloalkyl, aryl, heterocyclo, and heteroaryl are independently optionally substituted as valence allows with one or more R$_{18}$; R$_{15}$ and R$_{16}$ are each independently selected from hydrogen, alkyl, substituted alkyl, alkenyl, substituted alkenyl, cycloalkyl, aryl, heteroaryl, and heterocyclo; and R$_{18}$ is selected from hydrogen, halogen, hydroxyl, alkoxy, alkyl, substituted alkyl, alkenyl, substituted alkenyl, cycloalkyl, aryl, heteroaryl, and heterocyclo. More preferably, $R_{10}$ is selected from

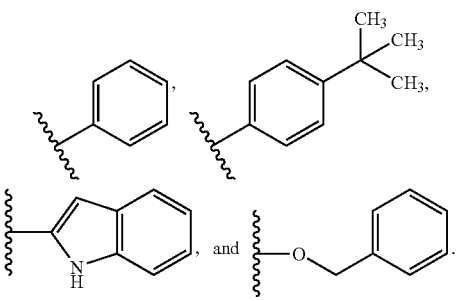

All aspects of the preferred compounds, including individual variable definitions, may be combined with other aspects to form other preferred compounds. For example, in one embodiment of the compounds of Formula (I) or (II), $R_1$ is hydrogen, $C_{1-4}$ alkyl, amino, or cyano, and $R_2$ may be selected from hydrogen, amino, and cyano. In another embodiment of the compounds of Formula (I) or (II), $R_1$ is hydrogen; $R_2$ may be substituted $C_{1-4}$ alkyl having one, two or three substituents selected from halo and amino In another embodiment of the compounds of Formula (I) or (II), $R_1$ is hydrogen; $R_2$ is selected from —C(=O)NR$_{11}$R$_{12}$, and —NR$_{11}$C(=O)R$_{12}$, wherein R$_{11}$ and R$_{12}$ are each independently selected from hydrogen, $C_{1-4}$alkyl, $C_{3-7}$cycloalkyl, aryl, heteroaryl, and heterocyclo.

In another embodiment of the compounds of Formula (I), $R_1$ is hydrogen; $R_2$ is selected from hydrogen, amino, and cyano; $R_4$ is substituted aryl optionally substituted with one or more of any substituents defined or exemplified herein. In a particular embodiment, $R_4$ is substituted phenyl.

In another embodiment of the compounds of Formula (I), $R_1$ is hydrogen; $R_2$ is substituted $C_{1-4}$ alkyl having one, two or three substituents selected from halo and amino; $R_4$ is substituted aryl.

In another embodiment of the compounds of Formula (I), $R_1$ is hydrogen; $R_2$ is selected from —C(=O)NR$_{11}$R$_{12}$, and —NR$_{11}$C(=O)R$_{12}$, wherein R$_{11}$ and R$_{12}$ are each independently selected from hydrogen, $C_{1-4}$alkyl, $C_{3-7}$cycloalkyl, aryl, heteroaryl, and heterocyclo; $R_4$ is substituted aryl.

In another embodiment of the compounds of Formula (II), $R_1$ is hydrogen; $R_2$ is selected from hydrogen, amino, and cyano; $R_8$ and $R_9$ are each independently hydrogen.

In another embodiment of the compounds of Formula (II), $R_1$ is hydrogen; $R_2$ is substituted $C_{1-4}$ alkyl having one, two or three substituents selected from halo and amino; $R_8$ and $R_9$ are each independently hydrogen.

In another embodiment of the compounds of Formula (II), $R_1$ is hydrogen; $R_2$ is selected from —C(=O)NR$_{11}$R$_{12}$, and —NR$_{11}$C(=O)R$_{12}$, wherein R$_{11}$ and R$_{12}$ are each independently selected from hydrogen, $C_{1-4}$alkyl, $C_{3-7}$cycloalkyl, aryl, heteroaryl, and heterocyclo; $R_8$ and $R_9$ are each independently hydrogen.

In another embodiment of the compounds of Formula (II), $R_1$ is hydrogen; $R_2$ is selected from hydrogen, amino, and cyano; $R_8$ and $R_9$ are each independently selected from $C_{1-4}$alkyl, heteroaryl and heterocyclo wherein said $C_{1-4}$alkyl, heteroaryl and heterocyclo are each optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —$C(O)OR_{13}$ wherein $R_{13}$ and $R_{14}$ are each independently selected from hydrogen, $C_{1-4}$alkyl, and heterocyclo.

In another embodiment of the compounds of Formula (II), $R_1$ is hydrogen; $R_2$ is substituted $C_{1-4}$ alkyl having one, two or three substituents selected from halo and amino; $R_8$ and $R_9$ are each independently selected from $C_{1-4}$alkyl, heteroaryl and heterocyclo wherein said $C_{1-4}$alkyl, heteroaryl and heterocyclo are each optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —$C(O)OR_{13}$ wherein $R_{13}$ and $R_{14}$ are each independently selected from hydrogen, $C_{1-4}$alkyl, and heterocyclo.

In another embodiment of the compounds of Formula (II), $R_1$ is hydrogen; $R_2$ is selected from —$C(=O)NR_{11}R_{12}$, and —$NR_{11}C(=O)R_{12}$, wherein $R_{11}$ and $R_{12}$ are each independently selected from hydrogen, $C_{1-4}$alkyl, $C_{3-7}$cycloalkyl, aryl, heteroaryl, and heterocyclo; $R_8$ and $R_9$ are each independently selected from $Cl_{1-4}$alkyl, heteroaryl and heterocyclo wherein said $C_{1-4}$alkyl, heteroaryl and heterocyclo are each optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —$C(O)OR_{13}$ wherein $R_{13}$ and $R_{14}$ are each independently selected from hydrogen, $C_{1-4}$alkyl, and heterocyclo.

In another embodiment of the compounds of Formula (II), $R_1$ is hydrogen; $R_2$ is selected from hydrogen, amino, and cyano; $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, wherein said heteroaryl and heterocyclo are independently optionally substituted as valence allows with one or more substituents selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —$O(C_{1-4}$alkyl), —$C(=O)H$, —$C(=O)$, —$S(C_{1-4}$alkyl), —$NH_2$, —$NH(C_{1-4}$alkyl), —$N(C_{1-4}$alkyl)$_2$, —NH(alkylene)$OR_{17}$ wherein $R_{17}$ is selected from hydrogen and $C_{1-4}$alkyl.

In another embodiment of the compounds of Formula (II), $R_1$ is hydrogen; $R_2$ is substituted $C_{1-4}$ alkyl having one, two or three substituents selected from halo and amino; $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, wherein said heteroaryl and heterocyclo are independently optionally substituted as valence allows with one or more substituents selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —$O(C_{1-4}$alkyl), —$C(=O)H$, —$C(=O)$, —$S(C_{1-4}$alkyl), —$NH_2$, —$NH(C_{1-4}$alkyl), —$N(C_{1-4}$alkyl)$_2$, —NH(alkylene)$OR_{17}$ wherein $R_{17}$ is selected from hydrogen and $C_{1-4}$alkyl.

In another embodiment of the compounds of Formula (II), $R_1$ is hydrogen; $R_2$ is selected from —$C(=O)NR_{11}R_{12}$, and —$NR_{11}C(=O)R_{12}$, wherein $R_{11}$ and $R_{12}$ are each independently selected from hydrogen, $C_{1-4}$alkyl, $C_{3-7}$cycloalkyl, aryl, heteroaryl, and heterocyclo; $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, wherein said heteroaryl and heterocyclo are independently optionally substituted as valence allows with one or more substituents selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —$O(C_{1-4}$alkyl), —$C(=O)H$, —$C(=O)$, —$S(C_{1-4}$alkyl), —$NH_2$, —$NH(C_{1-4}$alkyl), —$N(C_{1-4}$alkyl)$_2$, —NH(alkylene)$OR_{17}$ wherein $R_{17}$ is selected from hydrogen and $C_{1-4}$alkyl.

In another embodiment of the compounds of Formula (II), $R_1$ is hydrogen; $R_2$ is selected from hydrogen, amino, and cyano; $R_8$ and $R_9$ are each independently hydrogen; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{45}$, —$C(=O)R_{15}$, —$O—C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$; $R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo. In one preferred embodiment, $R_{10}$ is aryl optionally substituted with alkyl, preferably, tert-butyl. In another preferred embodiment, $R_{10}$ is optionally substituted bicyclic heteroaryl. Non-limiting examples of bicyclic heteroaryl are indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, and benzofuranyl In another embodiment of the compounds of Formula (II), $R_1$ is hydrogen; $R_2$ is substituted $C_{1-4}$ alkyl having one, two or three substituents selected from halo and amino; $R_8$ and $R_9$ are each independently hydrogen; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{15}$, —$C(=O)R_{15}$, —$O—C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$; $R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, $R_{10}$ is aryl optionally substituted with one or more of any substituents defined or exemplified herein. More preferably, the substituent is tert-butyl. In another preferred embodiment, $R_{10}$ is optionally substituted bicyclic heteroaryl.

In another embodiment of the compounds of Formula (II), $R_1$ is hydrogen; $R_2$ is selected from —$C(=O)NR_{11}R_{12}$, and —$NR_{11}C(=O)R_{12}$, wherein $R_{11}$ and $R_{12}$ are each independently selected from hydrogen, $C_{1-4}$alkyl, $C_{3-7}$cycloalkyl, aryl, heteroaryl, and heterocyclo; $R_8$ and $R_9$ are each independently hydrogen; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{15}$, —$C(=O)R_{15}$, —O—$C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$; $R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, $R_{10}$ is aryl optionally substituted with one or more of any substituents defined or exemplified herein. More preferably, the substituent is tert-butyl. In another preferred embodiment, $R_{10}$ is optionally substituted bicyclic heteroaryl.

In another embodiment of the compounds of Formula (II), $R_1$ is hydrogen; $R_2$ is selected from hydrogen, amino, and cyano; $R_8$ and $R_9$ are each independently selected from $C_{1-4}$alkyl, heteroaryl and heterocyclo wherein said $C_{1-4}$alkyl, heteroaryl and heterocyclo are each optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —$C(O)OR_{13}$ wherein $R_{13}$ and $R_{14}$ are each independently selected from hydrogen, $C_{1-4}$alkyl, and heterocyclo; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{15}$, —$C(=O)R_{15}$, —O—$C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$; $R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, $R_{10}$ is aryl optionally substituted with one or more of any substituents defined or exemplified herein. More preferably, the substituent is tert-butyl. In another preferred embodiment, $R_{10}$ is optionally substituted bicyclic heteroaryl.

In another embodiment of the compounds of Formula (II), $R_1$ is hydrogen; $R_2$ is substituted $C_{1-4}$ alkyl having one, two or three substituents selected from halo and amino; $R_8$ and $R_9$ are each independently selected from $C_{1-4}$alkyl, heteroaryl and heterocyclo wherein said $C_{1-4}$alkyl, heteroaryl and heterocyclo are each optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —$C(O)OR_{13}$ wherein $R_{13}$ and $R_{14}$ are each independently selected from hydrogen, $C_{1-4}$alkyl, and heterocyclo; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{15}$, —$C(=O)R_{15}$, —O—$C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$; $R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, $R_{10}$ is aryl optionally substituted with one or more of any substituents defined or exemplified herein. More preferably, the substituent is tert-butyl. In another preferred embodiment, $R_{10}$ is optionally substituted bicyclic heteroaryl.

In another embodiment of the compounds of Formula (II), $R_1$ is hydrogen; $R_2$ is selected from —$C(=O)NR_{11}R_{12}$, and —$NR_{11}C(=O)R_{12}$, wherein $R_{11}$ and $R_{12}$ are each independently selected from hydrogen, $C_{1-4}$alkyl, $C_{3-7}$cycloalkyl, aryl, heteroaryl, and heterocyclo; $R_8$ and $R_9$ are each independently selected from $C_{1-4}$alkyl, heteroaryl and heterocyclo wherein said $C_{1-4}$alkyl, heteroaryl and heterocyclo are each optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —$C(O)OR_{13}$ wherein $R_{13}$ and $R_{14}$ are each independently selected from hydrogen, $C_{1-4}$alkyl, and heterocyclo; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{15}$, —$C(=O)R_{15}$, —O—$C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$; $R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, $R_{10}$ is aryl optionally substituted with one or more of any substituents defined or exemplified herein. More preferably, the substituent is tert-butyl. In another preferred embodiment, $R_{10}$ is optionally substituted bicyclic heteroaryl. Non-limiting examples of bicyclic heteroaryl are indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, and benzofuranyl.

In another embodiment of the compounds of Formula (II), $R_1$ is hydrogen; $R_2$ is selected from hydrogen, amino, and cyano; $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, having from 1 to 4 heteroatoms selected from N, O, and S, wherein said heteroaryl or heterocyclo is any heteroaryl or heterocyclo defined or exemplified herein, optionally substituted with one or more of any substituents defined or exemplified herein. In a particular embodiment, the substituents on the heterocyclo formed by $R_8$ and $R_9$ are selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —O($C_{1-4}$alkyl), —C(=O)H, —C(=O), —S($C_{1-4}$alkyl), —NH$_2$, —NH($C_{1-4}$alkyl), —N($C_{1-4}$alkyl)$_2$, —NH(alkylene)OR$_{17}$ wherein $R_{12}$ is selected from hydrogen and $C_{1-4}$alkyl; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —OR$_{15}$, —NR$_{15}$R$_{16}$, —NR$_{15}$C(=O)R$_{16}$, —CO$_2$R$_{15}$, —C(=O)R$_{15}$, —O—C(=O)R$_{15}$, —C(=O)NR$_{15}$R$_{16}$, cycloalkyl, heterocyclo, aryl, and heteroaryl wherein said cycloalkyl, aryl, heterocyclo, and heteroaryl are independently optionally substituted as valence allows with one or more R$_{18}$; R$_{15}$ and R$_{16}$ are each independently selected from hydrogen, alkyl, substituted alkyl, alkenyl, substituted alkenyl, cycloalkyl, aryl, heteroaryl, and heterocyclo; and R$_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, R$_{10}$ is aryl optionally substituted with one or more of any substituents defined or exemplified herein. More preferably, the substituent is tert-butyl. In another preferred embodiment, R$_{10}$ is optionally substituted bicyclic heteroaryl.

In another embodiment of the compounds of Formula (II), $R_1$ is hydrogen; $R_2$ is substituted $C_{1-4}$ alkyl having one, two or three substituents selected from halo and amino; $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, having from 1 to 4 heteroatoms selected from N, O, and S, wherein said heteroaryl or heterocyclo is any heteroaryl or heterocyclo defined or exemplified herein, optionally substituted with one or more of any substituents defined or exemplified herein. In a particular embodiment, the substituents on the heterocyclo formed by $R_8$ and $R_9$ are selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —O($C_{1-4}$alkyl), —C(=O)H, —C(=O), —S($C_{1-4}$alkyl), —NH$_2$, —NH($C_{1-4}$alkyl), —N($C_{1-4}$alkyl)$_2$, —NH(alkylene)OR$_{17}$ wherein R$_{17}$ is selected from hydrogen and $C_{1-4}$ alkyl; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —OR$_{15}$, —NR$_{15}$R$_{16}$, —NR$_{15}$C(=O)R$_{16}$, —CO$_2$R$_{15}$, —C(=O)R$_{15}$, —O—C(=O)R$_{15}$, —C(=O)NR$_{15}$R$_{16}$, cycloalkyl, heterocyclo, aryl, and heteroaryl wherein said cycloalkyl, aryl, heterocyclo, and heteroaryl are independently optionally substituted as valence allows with one or more R$_{18}$; R$_{15}$ and R$_{16}$ are each independently selected from hydrogen, alkyl, substituted alkyl, alkenyl, substituted alkenyl, cycloalkyl, aryl, heteroaryl, and heterocyclo; and R$_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, R$_{10}$ is aryl optionally substituted with one or more of any substituents defined or exemplified herein. More preferably, the substituent is tert-butyl. In another preferred embodiment, R$_{10}$ is optionally substituted bicyclic heteroaryl.

In another embodiment of the compounds of Formula (II), $R_1$ is hydrogen; $R_2$ is selected from —C(=O)NR$_{11}$R$_{12}$, and —NR$_{11}$C(=O)R$_{12}$, wherein R$_{11}$ and R$_{12}$ are each independently selected from hydrogen, $C_{1-4}$ alkyl, $C_{3-7}$cycloalkyl, aryl, heteroaryl, and heterocyclo; $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, having from 1 to 4 heteroatoms selected from N, O, and S, wherein said heteroaryl or heterocyclo is any heteroaryl or heterocyclo defined or exemplified herein, optionally substituted with one or more of any substituents defined or exemplified herein. In a particular embodiment, the substituents on the heterocyclo formed by $R_8$ and $R_9$ are selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —O($C_{1-4}$alkyl), —C(=O)H, —C(=O), —S($C_{1-4}$alkyl), —NH$_2$, —NH($C_{1-4}$alkyl), —N($C_{1-4}$alkyl)$_2$, —NH(alkylene)OR$_{17}$ wherein R$_{17}$ is selected from hydrogen and $C_{1-4}$ alkyl; $R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —OR$_{15}$, —NR$_{15}$R$_{16}$, —NR$_{15}$C(=O)R$_{16}$, —CO$_2$R$_{15}$, —C(=O)R$_{15}$, —O—C(=O)R$_{15}$, —C(=O)NR$_{15}$R$_{16}$, cycloalkyl, heterocyclo, aryl, and heteroaryl wherein said cycloalkyl, aryl, heterocyclo, and heteroaryl are independently optionally substituted as valence allows with one or more R$_{18}$; R$_{15}$ and R$_{16}$ are each independently selected from hydrogen, alkyl, substituted alkyl, alkenyl, substituted alkenyl, cycloalkyl, aryl, heteroaryl, and heterocyclo; and R$_{18}$ is selected from hydrogen, halogen, hydroxyl, alkoxy, alkyl, substituted alkyl, alkenyl, substituted alkenyl, cycloalkyl, aryl, heteroaryl, and heterocyclo. Preferably, R$_{10}$ is aryl optionally substituted with one or more of any substituents defined or exemplified herein. More preferably, the substituent is tert-butyl. In another preferred embodiment, R$_{10}$ is optionally substituted bicyclic heteroaryl.

Methods of Preparation

Compounds of the present invention may be prepared by the exemplary processes described in the following reaction scheme. Exemplary reagents and procedures for these reactions appear hereinafter. Starting materials are commercially available or can be readily prepared by one of ordinary skill in the art. Modifications can be made to the methods of scheme by one skilled in the art using known methods. For all of the schemes, the groups $R_1$ and $R_2$ are as described herein for a compound of formula (I) or (II), unless otherwise indicated. Groups designated generally as X, as well as appropriate solvents, temperatures, pressures, starting materials (having the desired substituents) and other reaction conditions, may be readily selected by one of ordinary skill in the art. It is anticipated that, where possible, the products of the reaction schemes described below may be further elaborated by one of ordinary skill in the art.

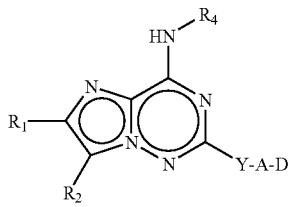

Compounds of general formula (I) may be prepared as described in Scheme A.

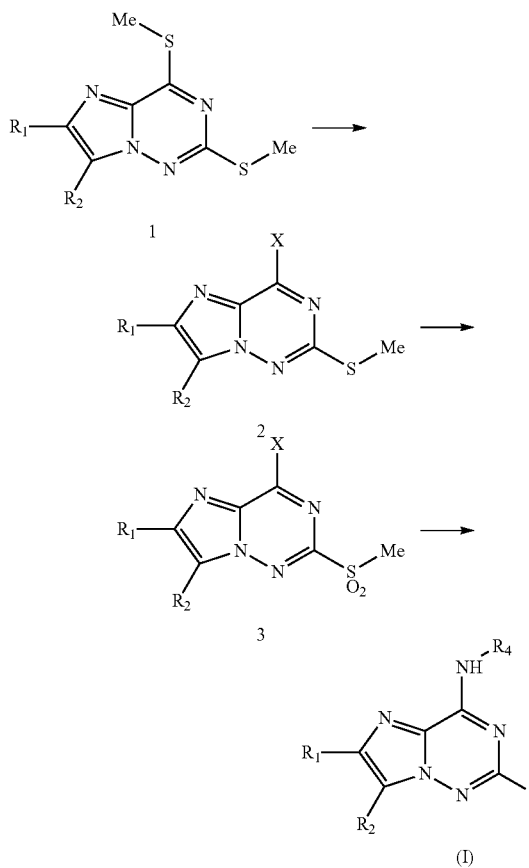

Treatment of imidazotriazine 1 with nucleophiles (such as anilines) in the presence of suitable base (such as potassium tert-butoxide) affords imidazotriazine 2. Treatment of imidazotriazine 2 with a suitable oxidizing agent (such as MCPBA) in a suitable solvent (such as DMF) provides imidazotriazine 3. Treatment of imidazotriazine 3 with a nucleophile (such as an amine) under either neat conditions or in a solvent (such as N-methylpryrrolidinone) provides imidazotriazine (I).

Utility

The compounds of the invention modulate kinase activity, including the modulation of Btk. Other types of kinase activity that may be modulated by the compounds of the instant invention include, but are not limited to, the Tec family of compounds, such as BMX, Btk, ITK, TXK and Tec, and mutants thereof.

Accordingly, compounds of formula (I) or (II) have utility in treating conditions associated with the modulation of kinase activity, and particularly the selective inhibition of Btk activity. Such conditions include B-cell mediated diseases in which cytokine levels are modulated as a consequence of intracellular signaling. Moreover, the compounds of formula (I) or (II) have advantageous selectivity for Btk activity over MK2 activity, preferably from at least 20 fold to over 1,000 fold more selective.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I) or (II) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

The present invention thus provides methods for treating such conditions, comprising administering to a subject in need thereof a therapeutically-effective amount of at least one compound of Formula (I) or (II) or a salt thereof. Therapeutically effective amount" is intended to include an amount of a compound of the present invention that is effective when administered alone or in combination to inhibit Btk.

The methods of treating Btk kinase-associated conditions may comprise administering compounds of Formula (I) or (II) alone or in combination with each other and/or other suitable therapeutic agents useful in treating such conditions. Accordingly, "therapeutically effective amount" is also intended to include an amount of the combination of compounds claimed that is effective to inhibit Btk. The combination of compounds is preferably a synergistic combination. Synergy, as described, for example, by Chou and Talalay, *Adv. Enzyme Regul.* 1984, 22:27-55, occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) or (II) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I) or (II) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of formula (I) or (II) as specified in the "Examples" section below, have been tested in one or more of the assays described below and have activity as inhibitors of Btk enzymes.

Biological Assays

Human Recombinant Btk Enzyme Assay

To V-bottom 384-well plates were added test compounds, human recombinant Btk (1 nM, Invitrogen Corporation), fluoresceinated peptide (1.5 μM), ATP (20 μM), and assay buffer (20 mM HEPES pH 7.4, 10 mM $MgCl_2$, 0.015% Brij35 and 4 mM DTT in 1.6% DMSO), with a final volume of 30 μL. After incubating at room temperature for 60 min, the reaction was terminated by adding 45 μl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required inhibiting 50% of kinase activity ($IC_{50}$). Compounds were dissolved at 10 mM in dimethylsulfoxide (DMSO) and evaluated at eleven concentrations.

Using this assay, the following $IC_{50}$ values derived by non-linear regression analysis were determined and compared to those values of certain compounds in US 2007/0078136 and US 2008/0045536. As seen in Table 1 below, the compounds of the instant invention as represented by Examples 11, 20, 28, and 32 show enhanced BTK inhibitory activities as compared to the previously reported compounds in US 2007/0078136 and US 2008/0045536.

TABLE 1

| Example Number | Structure | Human BTK ($IC_{50}$ uM) |
|---|---|---|
| 2 | 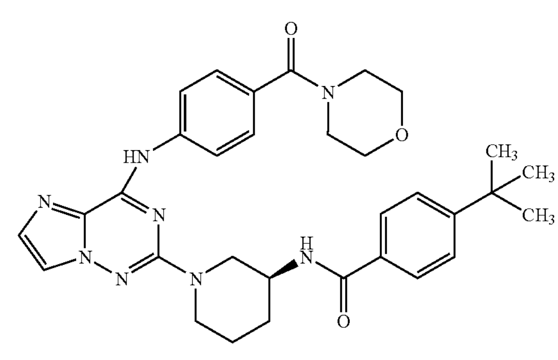 | 0.80 |

TABLE 1-continued
| Example Number | Structure | Human BTK (IC$_{50}$ uM) |
|---|---|---|
| 4 | 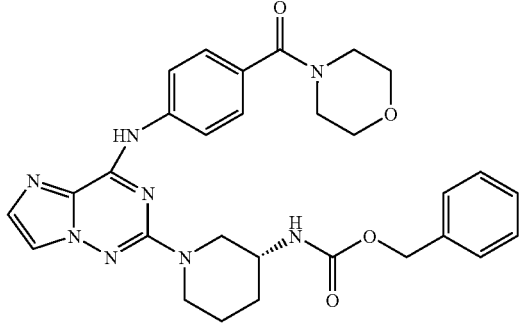 | 0.20 |
| 11 | 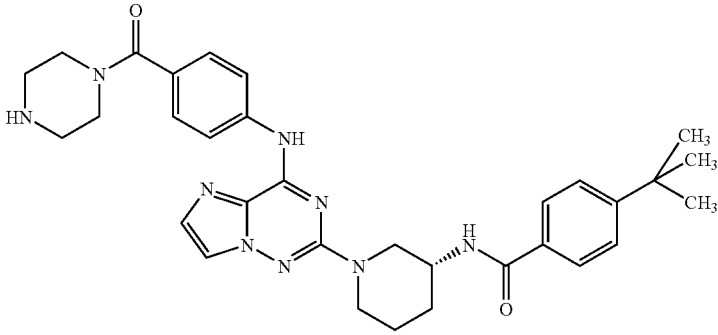 | 0.013 |
| 20 | 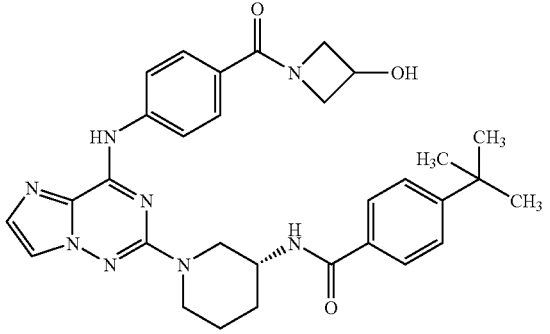 | 0.081 |
| 28 | 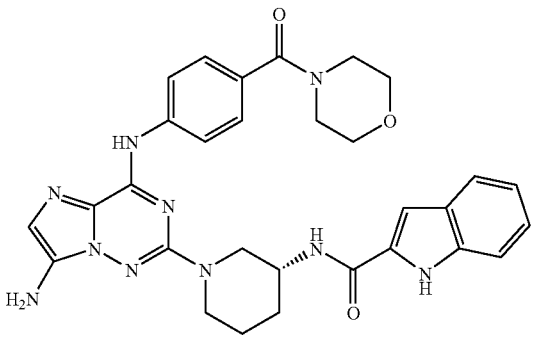 | 0.014 |

TABLE 1-continued

| Example Number | Structure | Human BTK (IC$_{50}$ uM) |
|---|---|---|
| 32 | 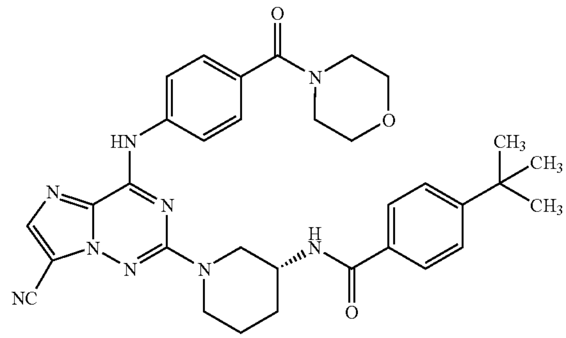 | 0.100 |
| Comparative Examples XIII in US 2007/0078136 | 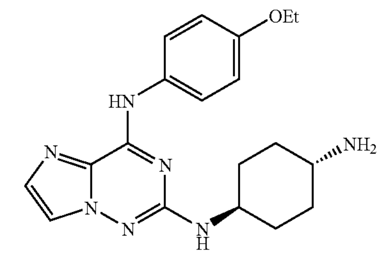 | 1.758 |
| I(159) in US 2008/0045536 | 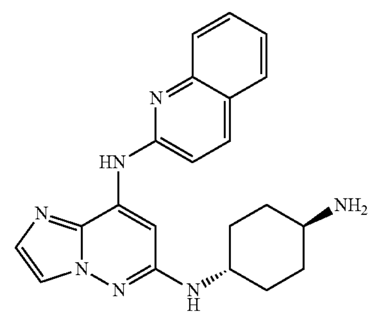 | 0.228 |
| III(18) in US 2008/0045536 | 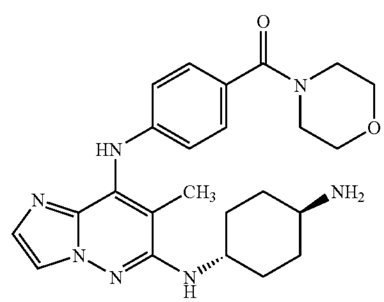 | >50.000 |
| V(10) in US 2008/0045536 | 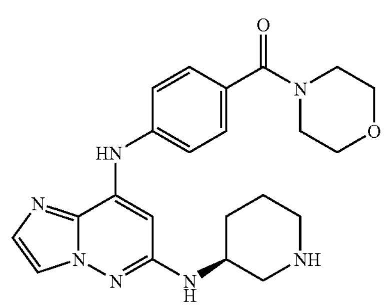 | 1.958 |

Mouse Splenic B Cell Proliferation Assay

Spleens from Balb/c mice (<12 weeks old) were mashed through screens and red blood cells were removed from splenocytes with RBC lysing buffer (Sigma-Aldrich Chemical Co, —St. Louis, Mo.). T cells were depleted by incubation on nylon wool columns (Wako, Richmond, Va.). Resulting splenic B cells prepared this way were routinely >90% $CD19^+$ as measured by FACS analysis. B cells ($1\times10^5$ cells per well) were added to serial dilutions of compounds in triplicate in 96-well flat-bottom plates in RPMI 1640 (Invitrogen, Grand Island, N.Y.), supplemented with 10% heat-inactivated fetal calf serum (FCS, Summit Biotechnology, Fort Collins, Colo.), containing 1% L-glutamine (Invitrogen), 50 ng/ml gentamicin (Invitrogen) and $5\times10^{-5}$M β-mercaptoethanol (Sigma-Aldrich). Cells were stimulated with 10 μg/ml of Affinipure $F(ab')_2$ fragment goat anti-mouse IgG IgM (Jackson Immunoresearch, West Grove, Pa.). Cultures were incubated for 72 hours, and pulsed for the last 6 hours with one μCi/well of $^3$[H]-thymidine (PerkinElmer, Boston, Mass.) prior to harvest on a Packard cell harvester (PerkinElmer), and counted by liquid scintillation on a Packard TopCount NXT (PerkinElmer). The most potent analogs were found to be below 1 μM. $IC_{50}$ values of representative compounds are shown in Table 2.

TABLE 2

| Example Number | Mouse Splenic B Cell Proliferation ($IC_{50}$ uM) |
|---|---|
| 13 | 0.056 |
| 26 | 0.080 |
| 32 | 0.31 |
| 10 | 0.33 |
| 30 | 0.98 |
| 9 | 1.29 |

Human Tonsillar B Cell Proliferation Assay

Tonsils were excised from patients undergoing routine tonsillectomy. Tonsil tissue was minced, mashed through screens and mononuclear cells were isolated on ficoll density gradients (Lymphocyte Separation Media; Mediatech Inc., Herndon, Va.). T cells were depleted from mononuclear cells by rosetting with sheep red blood cells (SRBC, Colorado Serum Company; Denver, Colo.). Tonsillar B cells prepared by this method were routinely >95% $CD19^+$ as measured by FACS analysis. B cells ($1\times10^5$ cells per well) were added to serial dilutions of compounds in triplicate in 96-well flat-bottom plates in RPMI 1640, (Invitrogen, Grand Island, N.Y.), supplemented with 10% heat-inactivated fetal calf serum (FCS, Summit Biotechnology, Fort Collins, Colo.), and containing antibiotic/antimycotic (Invitrogen, 1:100 dilution) and gentamicin (Invitrogen, 5 μg/ml). Cells were stimulated with 40 μg/ml AffinPure $F(ab')_2$ Fragment Goat anti Human IgG+IgM (Jackson Immunoresearch, West Grove, Pa.) in a total volume of 0.2 ml. Cultures were incubated for 72 hours, and pulsed for the last 6 hours with one μCi/well of $^3$[H]-thymidine (PerkinElmer, Boston, Mass.) prior to harvest on a Packard cell harvester (PerkinElmer), and counted by liquid scintillation on a Packard TopCount NXT (PerkinElmer). $IC_{50}$ values of representative compounds are shown in Table 3.

TABLE 3

| Example Number | Human Tonsillar B Cell Proliferation ($IC_{50}$ uM) |
|---|---|
| 5 | 0.037 |
| 1 | 0.097 |
| 6 | 0.17 |
| 36 | 0.45 |
| 12 | 1.58 |
| 9 | 1.91 |

Ramos FLIPR Assay

Ramos RA1 B cells (ATCC CRL-1596) at a density of $2\times10^6$ cells/ml in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, # 640177) and incubated at room temperature in the dark for 1 hour. Dye-loaded cells were pelleted (Beckmann GS-CKR, 1200 rpm, RT, 5 minutes) and resuspended in RT RPMI minus phenol red with 50 mM HEPES and 10% FBS to a density of $1\times10^6$ cells/ml. 150 μl aliquots (150,000/well) were plated into 96 well poly-D-lysine coated assay plates (BD 35 4640) and briefly centrifuged (Beckmann GS-CKR 800 rpm, 5 minutes, without brake). 50 μl compound dilutions in 0.4% DMSO/RPMI minus phenol red+50 mM HEPES+ 10% FBS were added to the wells and the plate was incubated at RT in the dark for 1 hour. Assay plate was briefly centrifuged as above prior to measuring calcium levels.

Using the FLIPR1 (Molecular devices), cells were stimulated by adding 50 μl 200 μg/ml $F(ab')_2$ anti-IgM/IgG (Jackson ImmunoResearch 109-006-127) diluted in 1X HBSS (Invitrogen 14025-076), 50 mM HEPES, 0.1% BSA. Changes in intracellular calcium concentrations were measured for 180 seconds and percent inhibition was determined relative to peak calcium levels seen in the presence of $F(ab')_2$ anti-IgM/IgG only. $IC_{50}$ values of representative compounds are shown in Table 4.

TABLE 4

| Example Number | Human Ramos Cell FLIPR ($IC_{50}$ uM) |
|---|---|
| 26 | 0.015 |
| 11 | 0.028 |
| 23 | 0.20 |
| 1 | 0.26 |
| 35 | 1.24 |
| 2 | 4.08 |

EXAMPLES

The following Examples illustrate embodiments of the inventive compounds and starting materials, and are not intended to limit the scope of the claims. For ease of reference, the following abbreviations are used herein:

ABBREVIATIONS

BOC=tert-butoxycarbonyl
bp=boiling point
Bu=butyl
DMAP=4-dimethylaminopyridine
DIPEA or DIEA=N,N-diisopropylethylamine
DME=1,2-dimethoxyethane
DMF=dimethyl formamide
DppF=1,1'-bis(diphenylphosphino)ferrocene EDCI=1-3-dimethylaminopropyl)-3-ethylcarbodiimide
Et=ethyl
Et$_2$O=diethyl ether
HOBT=1-hydroxybenzotriazole
EtOAc=ethyl acetate
EtOH=ethanol
g=gram(s)
H=hydrogen
l=liter
mCPBA=meta chloro perbenzoic acid
Me=methyl
MeCN=acetonitrile
MeOH=methanol
nM=nanomole
NMP=1-methyl-2-pyrrolidinone
Pd$_2$dba$_3$=tris(dibenzylideneacetone)dipalladium (0)
Ph=phenyl
Pr=propyl
PS=polystyrene
TEA=triethylamine
TFA=trifluoroacetic acid
mg=milligram(s)
ml or mL=milliliter
μl=microliter
mmol=mM=millimole
μmol=μM=micromole
mol=mole
mp=melting point
RT or rt=room temperature
HPLC=high pressure liquid chromatography
LC/MS=liquid chromatography/mass spectrometry Example 1

(R)-4-tert-Butyl-N-(1-(4-(4-(morpholine-4-carbonyl) phenylamino)imidazo[1,2-f][1,2,4]triazin-2-yl)piperidin-3-yl)benzamide

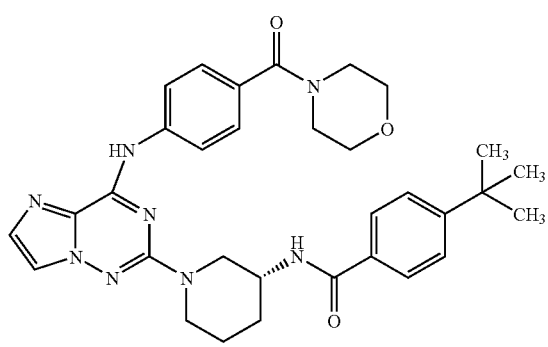

A. (R)-tert-Butyl 3-(4-tert-butylbenzamido)piperidine-1-carboxylate

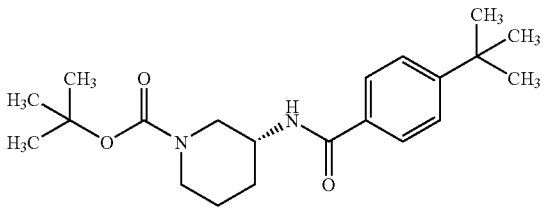

A mixture of 4-t-butylbenzoic acid (1.15 g, 6.45 mmol), (R)—N-BOC-3-aminopiperadine (1.00 g, 4.99 mmol), BOP (3.42 g, 7.73 mmol), and N-methylmorpholine (2.5 mL, 22.7 mmol) in DMF (10 mL) was stirred at rt for 2 hr and then heated at 55° C. for 3 hr. It was then diluted with ethyl acetate (150 mL), washed sequentially with water (3×50 mL) and brine (50 mL), and dried over anhydrous MgSO$_4$. Removal of solvent under vacuum provided a crude product of the titled compound, which was used in the next step without further purification.

B. (R)-4-tert-Butyl-N-(piperidin-3-yl)benzamide

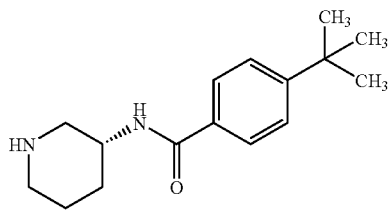

To a solution of the crude (R)-tert-Butyl 3-(4-tert-butylbenzamido)piperidine-1-carboxylate 4.99 mmol), obtained from the previous step, in CH$_2$Cl$_2$ (40 mL) at 0° C. was added TFA (40 mL) over 5 min. The mixture was stirred at rt for 1.5 hr. The volatiles were removed under vacuum. The residue was dissolved in ethyl acetate (200 mL), washed sequentially with saturated Na$_2$CO$_3$ solution (2×40 mL) and brine, and dried over anhydrous MgSO$_4$. The product was isolated by ISCO (80 g silica gel, 5-8% MeOH/CH$_2$Cl$_2$ containing 1% triethylamine)

The product thus obtained was found to be contaminated with 4-t-butylbenzoic acid. Therefore, it was dissolved in ethyl acetate (100 mL), washed sequentially with 1 N NaOH solution (2×30 mL), water and brine. The solution was dried over anhydrous MgSO$_4$. Removal of solvent under vacuum gave the desired product (1.00 g, 77% over two steps) as a white solid.

C. (4-(2-(Methylthio)imidazo[1,2-f][1,2,4]triazin-4-ylamino)phenyl)(morpholino)methanone

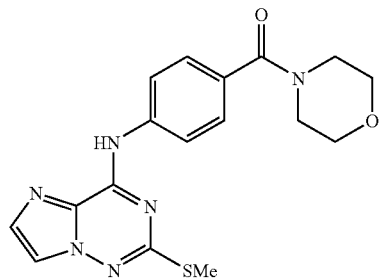

To a solution of (4-aminophenyl)(morpholino)methanone (1.05 g, 5.09 mmol) in THF (50 mL) was added potassium t-butoxide (1.0 M in THF, 10.5 mL, 10.5 mmol) at rt over 3 min. Then, 2,4-bis(methylthio)imidazo[1,2-f][1,2,4]triazine (1.20 g, 5.65 mmol), prepared as described in Journal of The Chemical Society, Perkins Transactions 1 1999, 20, 2929, was added at rt in one portion. The mixture was stirred at rt for 1 hr, and the reaction was quenched with ice-cold water (100 mL). The resulting solution was adjusted with 1 N HCl to pH 10. The product started to precipitate, and the first crop of product was collected by suction filtration. The filtrate was extracted with ethyl acetate (3×100 mL). The combined extract was washed with brine, and concentrated under vacuum to a volume of about 10 mL. The precipitating second crop of product was collected by suction filtration. The two crops of product (total 1.51 g, 80% yield) were combined and dried over Drierite® under vacuum.

D. (4-(2-(Methylsulfonyl)imidazo[1,2-f][1,2,4]triazin-4-ylamino)phenyl)(morpholino)methanone

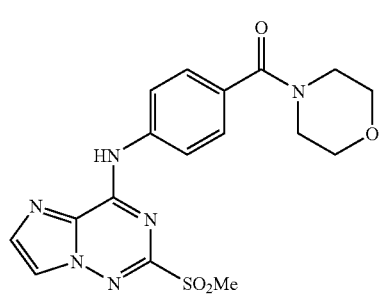

A solution of (4-(2-(Methylthio)imidazo[1,2-f][1,2,4]triazin-4-ylamino)phenyl)(morpholino)methanone (120 mg, 0.324 mmol) and mCPBA (77%, 236 mg, 0.971 mmol) in THF (10 mL) was stirred at rt for 1 hr. It was diluted with ethyl acetate (100 mL), washed sequentially with 5% $Na_2S_2O_3$ solution (2×30 mL), saturated $NaHCO_3$ solution (30 mL), and brine. The solution was dried over anhydrous $MgSO_4$. Removal of solvent under vacuum gave a crude product of the desired compound (128 mg) as a pale yellow solid, which was used in the next step without further purification.

E. (R)-4-tert-Butyl-N-(1-(4-(4-(morpholine-4-carbonyl)phenylamino)imidazo[1,2-f][1,2,4]triazin-2-yl)piperidin-3-yl)benzamide A mixture of (4-(2-(methylsulfonyl)imidazo[1,2-f][1,2,4]triazin-4-ylamino)phenyl)(morpholino)methanone (crude from the previous step, 60.0 mg, 0.152 mmol) and (R)-4-tert-butyl-N-(piperidin-3-yl)benzamide (97.0 mg, 0.372 mmol, 1B) in N-methyl-2-pyrrolidone (0.5 mL) was heated at 160° C. for 20 hr. It was diluted with MeOH (2 mL), divided into two portions, and injected to prep. HPLC. The correct fractions were combined, concentrated under vacuum, and basified with 1 N $NaHCO_3$ solution to pH 9. The precipitating product (25.8 mg, 29% yield) was collected as a beige solid by suction filtration and dried over $P_2O_5$ under vacuum. LCMS (M+H)$^+$=583.35. $^1$H NMR (500 MHz, DMSO-$d_6$) δ: 10.58 (1H, s), 8.27 (1H, d, J=7.70 Hz), 8.02 (2 H, d, J=8.25 Hz), 7.89 (1 H, s), 7.80 (2 H, d, J=8.25 Hz), 7.49 (1 H, d, J=7.7 Hz), 7.47 (2 H, d, J=8.80 Hz), 7.38 (2 H, d, J=8.80 Hz), 4.48 (1H, d, J=12.1 Hz)), 4.22 (1H, d, J=12.6 Hz)), 3.95 (1H, m), 3.50-3.39 (8H, m), 2.97-2.87 (2H, m), 1.94 (1H, m), 1.81 (1H, m), 1.70-1.56 (2H, m), 1.30 (9H, s).

Example 2

(S)-4-tert-Butyl-N-(1-(4-(4-(morpholine-4-carbonyl)phenylamino)imidazo[1,2-f][1,2,4]triazin-2-yl)piperidin-3-yl)benzamide

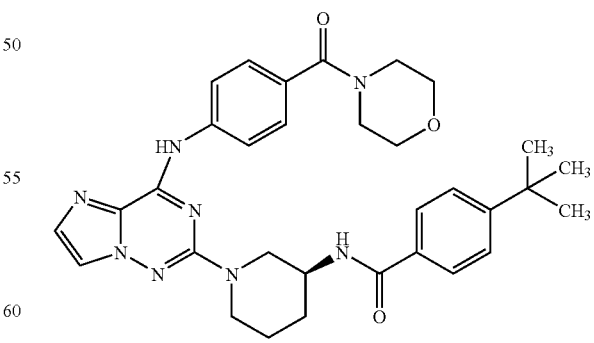

This compound was synthesized in the same manner as (R)-4-tert-Butyl-N-(1-(4-(4-(morpholine-4-carbonyl)phenylamino)imidazo[1,2-f][1,2,4]triazin-2-yl)piperidin-3-yl)benzamide (Example 1) was synthesized. LCMS (M+H)+ =583.35.

Example 3

(R)—N-(1-(4-(4-(Morpholine-4-carbonyl)phenylamino)imidazo[1,2-f][1,2,4]triazin-2-yl)piperidin-3-yl)-1H-indole-2-carboxamide

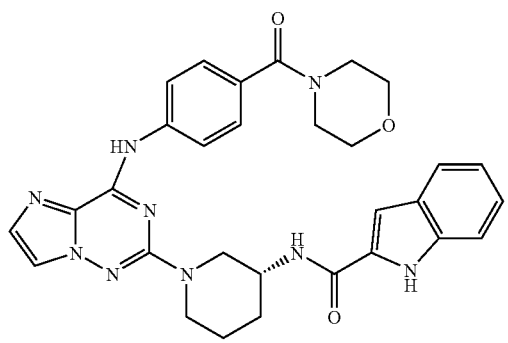

This compound was synthesized in the same manner as (R)-4-tert-Butyl-N-(1-(4-(4-(morpholine-4-carbonyl)phenylamino)imidazo[1,2-f][1,2,4]triazin-2-yl)piperidin-3-yl)benzamide (Example 1) was synthesized. LCMS (M+H)+= 566.17. $^1$H NMR (500 MHz, DMSO-$d_6$) δ: 11.61 (1H, s), 10.58 (1H, s), 8.35 (1 H, d, J=7.70 Hz), 8.00 (2 H, d, J=8.25 Hz), 7.90 (1 H, s), 7.60 (1 H, d, J=7.70 Hz), 7.50 (1H, s), 7.44 (1 H, d, J=8.25 Hz), 7.38 (2 H, d, J=8.25 Hz), 7.14-7.22 (2 H, m), 7.03 (1H, t, J=7.42 Hz), 4.48 (1H, d, J=9.3 Hz), 4.25 (1H, d, J=12.6 Hz), 4.01 (1H, m), 3.48-3.42 (8H, m), 3.00-2.89 (2H, m), 1.99 (1H, m), 1.84 (1H, m), 1.70-1.57 (2H, m).

Example 4

(R)-Benzyl 1-(4-(4-(morpholine-4-carbonyl)phenylamino)imidazo[1,2-f][1,2,4]triazin-2-yl)piperidin-3-ylcarbamate

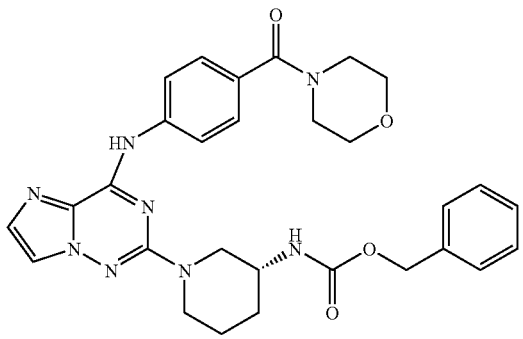

A mixture of (4-(2-(methylsulfonyl)imidazo[1,2-f][1,2,4]triazin-4-ylamino)phenyl)(morpholino)methanone (100 mg, 0.248 mmol, Example 1D) and (R)-3-N-Cbz-aminopiperidine (145 mg, 0.619 mmol) in N-methyl-2-pyrrolidone (0.5 mL) was heated at 150° C. for 40 hr. It was diluted with MeOH (3.5 mL), divided into three portions, and injected to prep. HPLC. The correct fractions were combined, concentrated under vacuum, basified with saturated NaHCO$_3$ solution to pH 9, and extracted with ethyl acetate (2×30 mL). The combined extract was dried over anhydrous MgSO$_4$. Removal of solvent under vacuum gave the desired compound (9.1 mg, 6.6% yield) as a pale yellow solid. LCMS (M+H)+=557.23. $^1$H NMR (500 MHz, DMSO-$d_6$) δ: 10.62 (1H, s), 8.11 (2H, d, J=8.2 Hz), 7.95 (1H, s), 7.57 (1H, s), 7.51-7.47 (3H, m), 7.41-7.37 (5H, m), 5.10 (2H, s), 4.40 (1H, dd, J=12.4, 3.6 Hz), 4.14 (1H, d, J=13.2 Hz), 3.64-3.55 (9H, m), 3.08 (1H, m), 2.98 (1H, m), 1.97 (1H, m), 1.85 (1H, m), 1.59-1.52 (2H, m).

Example 5

(R)-4-tert-Butyl-N-(1-(4-(4-(4-methylpiperazine-1-carbonyl)phenylamino)imidazo[1,2-f][1,2,4]triazin-2-yl)piperidin-3-yl)benzamide

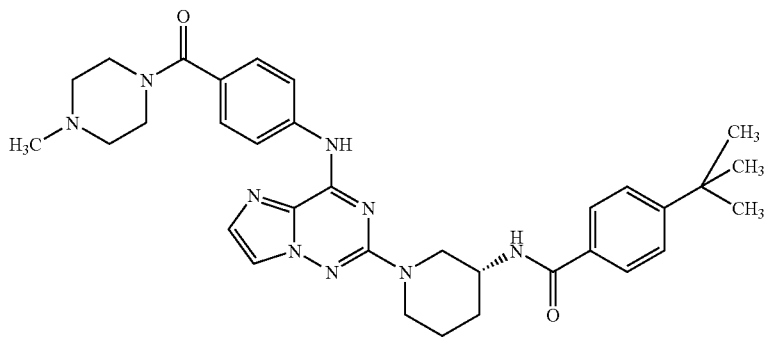

A. Ethyl 4-(2-(methylthio)imidazo[1,2-f][1,2,4]triazin-4-ylamino)benzoate

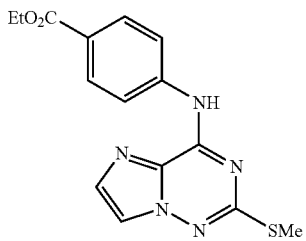

To a solution of 2,4-bis(methylthio)imidazo[1,2-f][1,2,4]triazine (2.5053 g, 11.8 mmol) and ethyl 4-aminobenzoate (1.6285 g, 9.86 mmol) in THF (50 mL) at 0° C. under nitrogen was added KOtBu (1M in THF; 22 mL, 22 mmol) over 8 min. The cold bath was removed, and the reaction was stirred to room temperature for 15 min. It was diluted with EtOAc and washed with water and brine, successively; dried over Na$_2$SO$_4$, filtered and concentrated in vacuo. Trituration with EtOAc followed by Et$_2$O afforded the title compound as a faintly yellow solid (2.8311 g, 87%). LC/MS (M+H)=330.07.

B. Ethyl 4-(2-(methylsulfonyl)imidazo[1,2-f][1,2,4]triazin-4-ylamino)benzoate

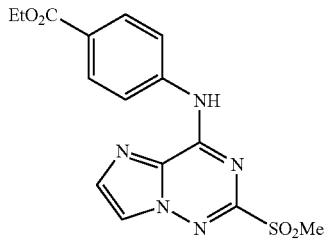

To a solution of ethyl 4-(2-(methylthio)imidazo[1,2-f][1,2,4]triazin-4-ylamino)benzoate (1.0187 g, 3.1 mmol) in THF (10.5 mL) under nitrogen was added MCPBA (71%; 2.27 g, 9.3 mmol) and stirred overnight. The reaction mixture was diluted with EtOAc and washed with 5% aq. Na$_2$S$_2$O$_3$, saturated aq. NaHCO$_3$ and brine, successively; dried over Na$_2$SO$_4$, filtered and concentrated in vacuo. Trituration with EtOAc afforded the title compound as a faintly yellow solid (0.8771 g, 78%). LC/MS (M+H)=362.12.

C. (R)-Ethyl 4-(2-(3-(4-tert-butylbenzamido)piperidin-1-yl)imidazo[1,2-f]-[1,2,4]triazin-4-ylamino)benzoate

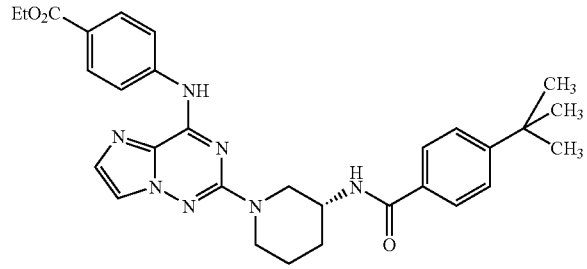

A solution of ethyl 4-(2-(methylsulfonyl)imidazo[1,2-f][1,2,4]triazin-4-ylamino)benzoate (0.8112 g, 2.2 mmol) and (R)-4-tert-butyl-N-(piperidin-3-yl)benzamide (1.4811 g, 5.7 mmol) in NMP (7.5 mL) was heated in a sealed tube at 160° C. for 4 days. After cooling to room temperature, it was diluted with EtOAc and washed with water and brine, successively; dried over Na$_2$SO$_4$, filtered and concentrated in vacuo. Purification by flash chromatography on a 120 g ISCO column eluted with 0-4.5% MeOH/CH$_2$Cl$_2$ and trituration with Et$_2$O afforded the title compound as a light tan solid (0.7530 g, 62%). LC/MS (M+H)=542.24.

D. (R)-4-(2-(3-(4-tert-Butylbenzamido)piperidin-1-yl)imidazo[1,2-f][1,2,4]triazin-4-ylamino)benzoic acid

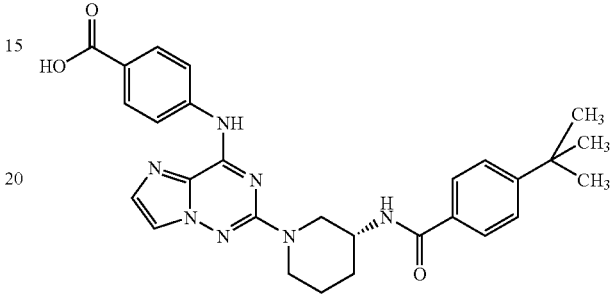

A solution of (R)-ethyl 4-(2-(3-(4-tert-butylbenzamido)piperidin-1-yl)imidazo[1,2-f][1,2,4]triazin-4-ylamino)benzoate (1.2889 g, 2.4 mmol) and NaOH (1 N in H$_2$O; 9.52 ml, 9.5 mmol) in MeOH (5 ml) was refluxed for 3 h and then cooled to room temperature. It was concentrated in vacuo not to dryness. At 0° C., aqueous HCl (1N) was added until pH ~6-7 by litmus paper, and the solution was extracted by CH$_2$Cl$_2$ (2×). The organic layers were combined, dried over Na$_2$SO$_4$, filtered, and concentrated in vacuo. Trituration with CH$_2$Cl$_2$ provided the title compound as a light tan solid (0.6772 g, 55%). LC/MS (M+H)=514.19; $^1$H NMR (500 MHz, d6-DMSO) δ ppm 1.29 (s, 9H), 1.53-1.72 (m, 2H), 1.84 (m, 1H), 1.96 (m, 1H), 2.89 (m, 1H), 2.96 (m, 1H), 3.95 (m, 1H), 4.22 (d, J=12.65 Hz, 1H), 4.49 (d, J=9.90 Hz, 1H), 7.46 (d, J=8.25 Hz, 2 H) 7.51 (s, 1 H) 7.82 (d, J=8.25 Hz, 2 H) 7.90 (s, 1 H) 7.95 (d, J=8.80 Hz, 2 H) 8.08 (d, J=8.80 Hz, 2 H) 8.26 (d, J=7.70 Hz, 1 H), 10.67 (s, 1H).

E. (R)-4-tert-Butyl-N-(1-(4-(4-(4-methylpiperazine-1-carbonyl)phenylamino)imidazo[1,2-f][1,2,4]triazin-2-yl)piperidin-3-yl)benzamide A solution of (R)-4-(2-(3-(4-tert-butylbenzamido)piperidin-1-yl)imidazo[1,2-f][1,2,4]triazin-4-ylamino)benzoic acid (0.034 g, 0.066 mmol), 1-methylpiperazine (9.95 mg, 0.099 mmol), HOBT (0.015 g, 0.099 mmol), EDC (0.019 g, 0.099 mmol) and DIPEA (0.035 ml, 0.199 mmol) in DMF (0.5 mL) in a sealed vial was mechanically shaken at 65° C. overnight. After cooling to room temperature, the reaction was diluted with MeOH (1 mL) and subjected to autoprep HPLC. The appropriate fractions were collected; NaHCO$_3$ (solid) was added, and the fractions were concentrated in vacuo not to dryness. It was extracted with CH$_2$Cl$_2$ (3×); the organic layers were combined, dried over Na$_2$SO$_4$, filtered and concentrated in vacuo to give (R)-4-tert-butyl-N-(1-(4-(4-(4-methylpiperazine-1-carbonyl)phenylamino)imidazo[1,2-f][1,2,4]triazin-2-yl)piperidin-3-yl)benzamide (21.6 mg, 0.036 mmol, 54.8% yield) as an off-white solid. LC/MS (M+H)=596.30; 1H NMR (d6-DMSO) δ ppm 1.37 (s, 9H), 1.59-1.79 (m, 2H), 1.88 (m, 1H), 2.02 (m, 1H), 2.22 (s, 3H), 2.26-2.39 (m, 4H), 2.92-3.06 (m, 2H), 3.48-3.65 (m, 4H), 4.02 (m, 1H), 4.30 (d, J=12.65 Hz, 1H), 4.57 (d, J=9.90 Hz, 1H), 7.43 (d, J=8.25 Hz, 2 H), 7.54 (d, J=8.25 Hz, 2 H), 7.57 (s, 1 H), 7.87 (d, J=8.25 Hz, 2 H), 7.96 (s, 1 H), 8.09 (d, J=8.80 Hz, 2 H), 8.33 (d, J=7.70 Hz, 1 H), 10.63 (s, 1H).

Example 6

(R)-4-tert-Butyl-N-(1-(4-(4-(4-(2-hydroxyethyl)piperazine-1-carbonyl)phenylamino)imidazo[1,2-f][1,2,4]triazin-2-yl)piperidin-3-yl)benzamide

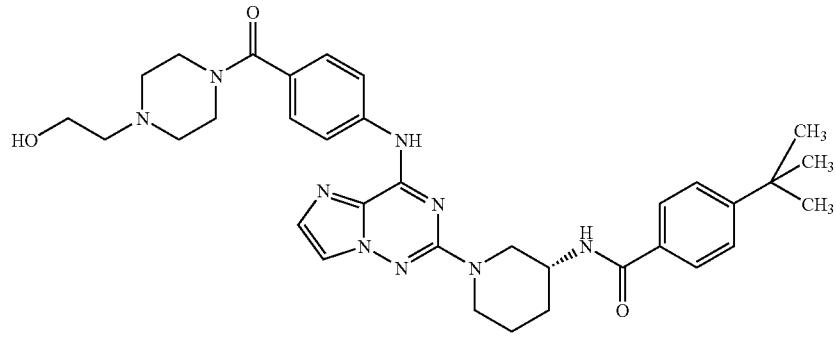

Following the procedure for Example 5, the title compound was obtained. LC/MS (M+H)=626.29; $^1$H NMR (500 MHz, d6-DMSO) δ ppm 1.25 (s, 9H), 1.47-1.66 (m, 2H), 1.77 (m, 1H), 1.90 (m, 1H), 2.23-2.40 (m, 6H), 2.81-2.96 (m, 2H), 3.38-3.51 (m, 6H), 3.90 (m, 1H), 4.17 (d, J=12.65 Hz, 1H), 4.37 (t, J=5.22 Hz, 1H), 4.43 (d, J=9.90 Hz, 1H), 7.32 (d, J=8.80 Hz, 2 H), 7.42 (d, J=8.25 Hz, 2 H), 7.45 (s, 1 H), 7.75 (d, J=8.25 Hz, 2 H), 7.84 (s, 1 H), 7.97 (d, J=8.80 Hz, 2 H), 8.21 (d, J=7.70 Hz, 1 H), 10.51 (s, 1H).

Example 7

(R)-4-tert-Butyl-N-(1-(4-(4-(2-hydroxyethylcarbamoyl)phenylamino)imidazo[1,2-f][1,2,4]triazin-2-yl)piperidin-3-yl)benzamide

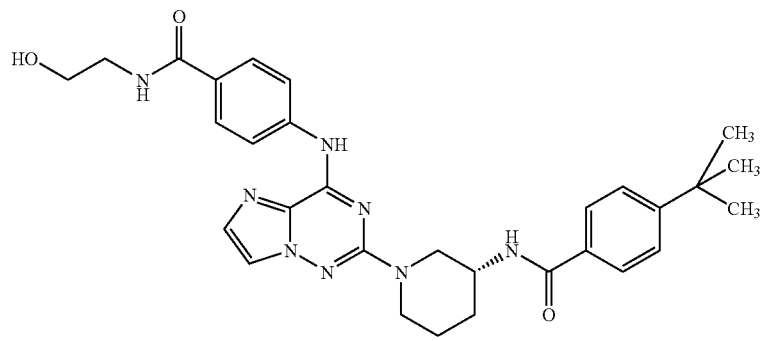

Following the procedure for Example 5, the title compound was obtained. LC/MS (M+H)=557.31; $^1$H NMR (500 MHz, d6-DMSO) δ ppm 1.29 (s, 9H), 1.52-1.73 (m, 2H), 1.84 (m, 1H), 1.96 (m, 1H), 2.90-3.04 (m, 2H), 3.50 (q, J=6.05 Hz, 2H), 3.95 (m, 1H), 4.23 (d, J=13.20 Hz, 1H), 4.43 (dd, J1=3.57, J2=12.37 Hz, 1H), 4.71 (t, J=5.77 Hz 1H), 7.46 (d, J=8.25 Hz, 2 H) 7.50 (s, 1 H) 7.80 (d, J=8.80 Hz, 2 H) 7.85 (d, J=8.80 Hz, 2 H) 7.89 (s, 1 H) 8.03 (d, J=8.80 Hz, 2 H) 8.25 (d, J=7.70 Hz, 1 H) 8.32 (t, J=5.77 Hz, 1 H), 10.55 (s, 1H).

Example 8

(R)-4-tert-Butyl-N-(1-(4-(4-(4-hydroxypiperidine-1-carbonyl)phenylamino)imidazo[1,2-f][1,2,4]triazin-2-yl)piperidin-3-yl)benzamide

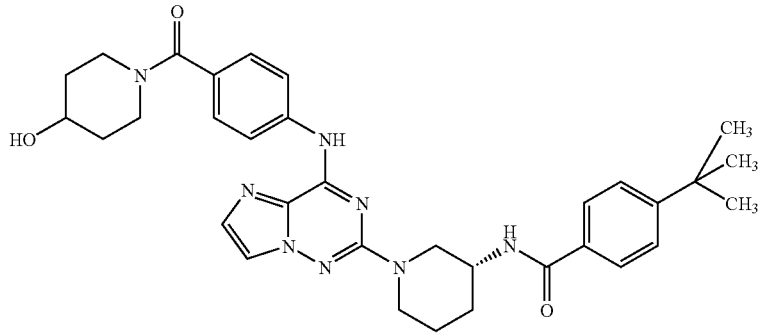

Following the procedure for Example 5, the title compound was obtained. LC/MS (M+H)=597.35; $^1$H NMR (500 MHz, d6-DMSO) δ ppm 1.28 (s, 9H), $^1$H NMR (500 MHz, d6-DMSO) δ ppm 1.28 (s, 9H), 1.50-1.75 (m, 6H), 1.81 (m, 1H), 1.92 (m, 1H), 2.82-2.97 (m, 2H), 3.11 (m, 1H), 3.41-3.53 (m, 4H), 3.67 (m, 1H), 3.93 (m, 1H), 4.20 (d, J=12.65 Hz, 1H), 4.46 (d, J=10.45 Hz, 1H), 7.33 (d, J=8.25 Hz, 2H), 7.45 (d, J=8.80 Hz, 2 H), 7.48 (s, 1 H), 7.78 (d, J=8.25 Hz, 2 H), 7.86 (s, 1H), 7.98 (d, J=8.25 Hz, 2 H), 8.24 (d, J=7.70 Hz, 1 H), 10.53 (s, 1H).

Example 9

4-tert-Butyl-N—((R)-1-(4-(4-((S)-pyrrolidin-3-ylcarbamoyl)phenylamino)imidazo[1,2-f][1,2,4]triazin-2-yl)piperidin-3-yl)benzamide

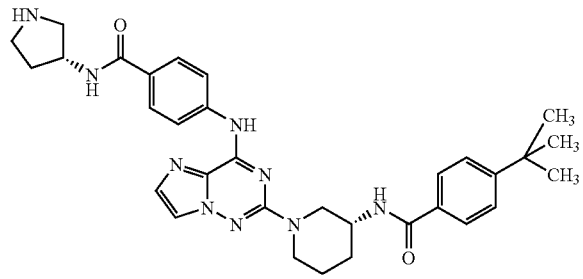

A. (S)-tert-Butyl 3-(4-(2-((R)-3-(4-tert-butylbenzamido)piperidin-1-yl)imidazo[1,2-f][1,2,4]triazin-4-ylamino)benzamido)pyrrolidine-1-carboxylate

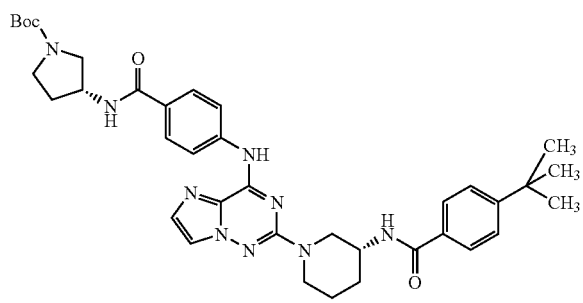

Following the procedure for Example 5, the title compound was obtained as a light tan solid. LC/MS (M+H)=682.36.

B. 4-tert-Butyl-N—((R)-1-(4-(4-((S)-pyrrolidin-3-ylcarbamoyl)phenylamino)imidazo[1,2-f][1,2,4]triazin-2-yl)piperidin-3-yl)benzamide To a solution of (S)-tert-butyl 3-(4-(2-((R)-3-(4-tert-butylbenzamido)piperidin-1-yl)imidazo[1,2-f][1,2,4]triazin-4-ylamino)benzamido)pyrrolidine-1-carboxylate (0.0174 g, 0.026 mmol) in $CH_2Cl_2$ (0.5 ml) under nitrogen at 0° C. was added TFA (0.029 mL, 0.383 mmol). After 5 min, the ice-water bath was removed, and the reaction was stirred to room temperature for 1.5 h. After concentrating in vacuo, the residue was diluted with MeOH (1 mL) and subjected to autoprep HPLC. The appropriate fractions were collected; $NaHCO_3$ (solid) was added, and the fractions were concentrated in vacuo not to dryness. It was extracted with $CH_2Cl_2$ (3×); the organic layers were combined, dried over $Na_2SO_4$, filtered and concentrated in vacuo to give the title compound (7.6 mg, 0.013 mmol, 51.2% yield) as a white solid. LC/MS (M+H)= 582.37.

Example 10

(R)-4-tert-Butyl-N-(1-(4-(4-carbamoylphenylamino)imidazo[1,2-f][1,2,4]triazin-2-yl)piperidin-3-yl)benzamide

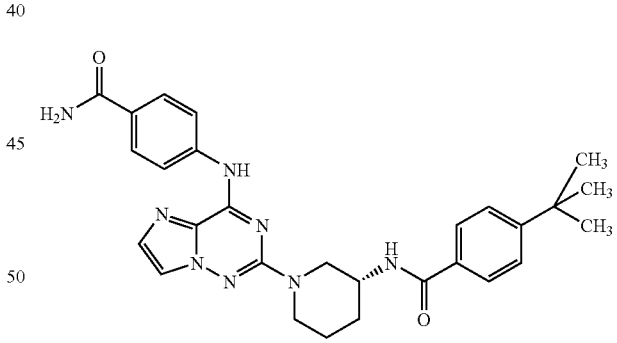

To (R)-4-(2-(3-(4-tert-butylbenzamido)piperidin-1-yl)imidazo[1,2-f][1,2,4]triazin-4-ylamino)benzoic acid (0.0295 g, 0.057 mmol, Example 5D) at 0° C. under nitrogen was added thionyl chloride (0.5 mL, 6.85 mmol). After 1 h, the reaction was concentrated in vacuo to give crude acid chloride. To this chloride at 0° C. was added ammonium hydroxide (14.8 M in water, 1.0 mL, 14.80 mmol), and the cold bath was removed. The solution was stirred overnight to room temperature. The insoluble crude product was collected by filtration and washed with water. It was dissolved in MeOH (1 mL) and subjected to autoprep HPLC. The appropriate fractions were collected; $NaHCO_3$ (solid) was added, and the fractions were concentrated in vacuo not to dryness. It was extracted with $CH_2Cl_2$ (3×); the organic layers were combined, dried over $Na_2SO_4$, filtered and concentrated in vacuo to give the title compound as a light tan solid (8.2 mg, 27.9%). LC/MS (M+H)=513.18; $^1$H NMR (500 MHz, d6-DMSO) δ ppm 1.29 (s, 9H), 1.51-1.71 (m, 2H), 1.83 (m, 1H), 1.94 (m, 1H), 2.89-3.02 (m, 2H), 3.94 (m, 1H), 4.22 (d, J=13.20 Hz, 1H), 4.42 (dd, J1=3.85, J2=12.65 Hz, 1H), 7.24 (s, 1 H) 7.45 (d, J=8.80 Hz, 2 H) 7.49 (s, 1 H) 7.80 (d, J=8.80 Hz, 2 H) 7.84-7.87 (m, 2 H) 7.88 (d, J=2.75 Hz, 2 H) 8.02 (d, J=8.80 Hz, 2H) 8.24 (d, J=7.70 Hz, 1 H), 10.55 (s, 1H).

Example 11

(R)-4-tert-Butyl-N-(1-(4-(4-(piperazine-1-carbonyl)phenylamino)imidazo[1,2-f][1,2,4]triazin-2-yl)piperidin-3-yl)benzamide

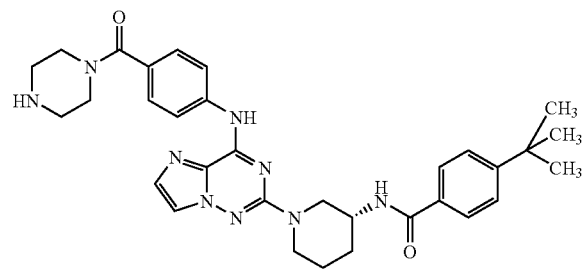

A. (R)-tert-Butyl 4-(4-(2-(3-(4-tert-butylbenzamido)piperidin-1-yl)imidazo[1,2-f][1,2,4]-triazin-4-ylamino)benzoyl)piperazine-1-carboxylate

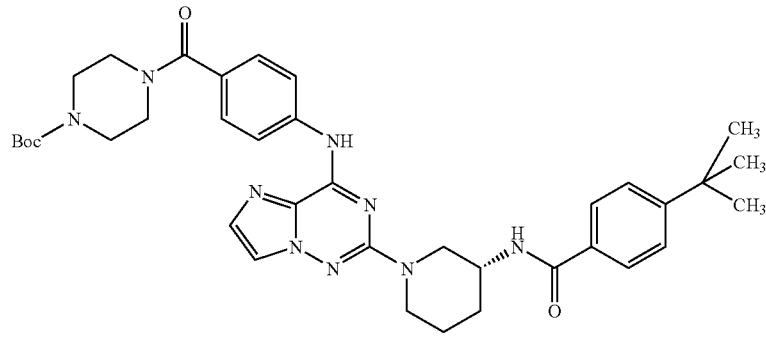

Following the procedure for Example 5, the title compound was obtained as a light tan solid. LC/MS (M+H)=682.32.

B. (R)-4-tert-Butyl-N-(1-(4-(4-(piperazine-1-carbonyl)phenylamino)imidazo[1,2-f][1,2,4]triazin-2-yl)piperidin-3-yl)benzamide Following Step B of Example 9, the title compound was obtained as an off-white solid. LC/MS (M+H)=582.26; $^1$H NMR (500 MHz, d6-DMSO) δ ppm 1.37 (s, 9H), 1.61-1.77 (m, 2H), 1.89 (m, 1H), 2.01 (m, 1H), 2.65-2.75 (m, 4H), 2.88-3.12 (m, 2H), 3.24-3.57 (m, 4H), 4.03 (m, 1H), 4.29 (d, J=12.65 Hz, 1H), 4.54 (d, J=12.65 Hz, 1H), 7.42 (d, J=8.25 Hz, 2 H) 7.54 (d, J=8.25 Hz, 2 H) 7.57 (s, 1 H) 7.87 (d, J=8.80 Hz, 2 H) 7.95 (s, 1 H) 8.08 (d, J=8.25 Hz, 2 H) 8.33 (d, J=7.70 Hz, 1 H), 10.62 (s, 1H).

Example 12

4-tert-Butyl-N—((R)-1-(4-(4-((R)-pyrrolidin-3-ylcarbamoyl)phenylamino)imidazo[1,2-f][1,2,4]triazin-2-yl)piperidin-3-yl)benzamide

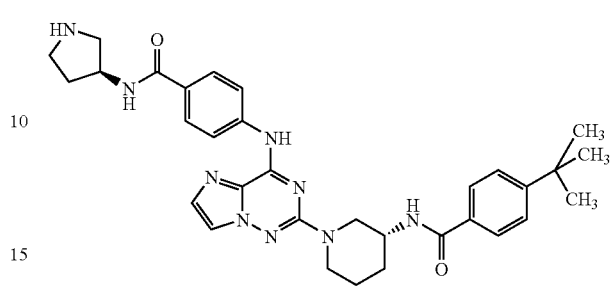

A. (R)-tert-Butyl 3-(4-(2-((R)-3-(4-tert-butylbenzamido)piperidin-1-yl)imidazo[1,2-f][1,2,4]triazin-4-ylamino)benzamido)pyrrolidine-1-carboxylate

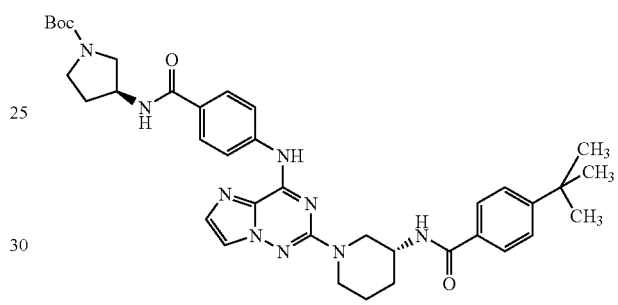

Following the procedure for Example 5, the title compound was obtained as a light tan solid. LC/MS (M+H)=682.29.

B. 4-tert-Butyl-N—((R)-1-(4-(4-((R)-pyrrolidin-3-ylcarbamoyl)phenylamino)imidazo[1,2-f][1,2,4]triazin-2-yl)piperidin-3-yl)benzamide Following Step B of Example 9, the title compound was obtained as a light tan solid. LC/MS (M+H)=582.27; $^1$H NMR (500 MHz, d6-DMSO) δ ppm 1.29 (s, 9H), 1.53-1.71 (m, 3H), 1.83 (m, 1 H), 1.90-2.00 (m, 2 H), 2.64 (m, 1 H), 2.74 (m, 1 H), 2.84-3.03 (m, 4 H) 3.94 (m, 1 H), 4.19-4.34 (m, 2 H), 4.46 (d, J=12.65 Hz, 1 H), 7.46 (d, J=8.25 Hz, 2 H) 7.50 (s, 1 H) 7.82 (dd, J=14.30, 8.80 Hz, 4 H) 7.89 (s, 1 H) 8.04 (d, J=8.80 Hz, 2 H) 8.24 (dd, J=10.17, 7.42 Hz, 2 H).

Following the procedures that were used to synthesize examples 5-12, additional compounds were prepared, which are shown in Table 5.

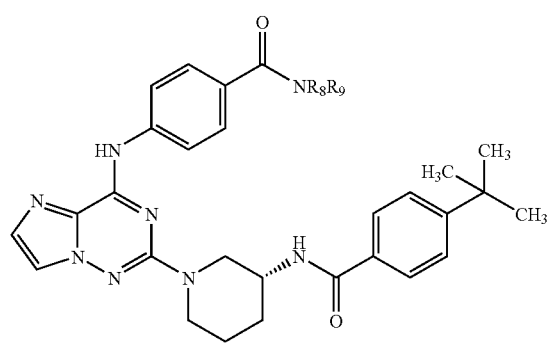

TABLE 5

| Example | NR₈R₉ | M + H |
|---------|-------|-------|
| 13 | (S)-tetrahydrofuran-3-ylamino | 583.28 |
| 14 | (S)-3-hydroxypyrrolidin-1-yl | 583.27 |
| 15 | (R)-3-hydroxypyrrolidin-1-yl | 583.26 |
| 16 | methyl (S)-serinate-N | 615.34 |
| 17 | (3R,4R)-3,4-dihydroxypyrrolidin-1-yl | 599.31 |
| 18 | N-methyl-N-(2-hydroxyethyl)amino | 571.27 |
| 19 | 3-aminoazetidin-1-yl | 568.28 |
| 20 | 3-hydroxyazetidin-1-yl | 569.25 |

TABLE 5-continued

| Example | NR₈R₉ | M + H |
|---------|-------|-------|
| 21 | 3-(2-hydroxyethylamino)azetidin-1-yl | 612.36 |
| 22 | (S)-3-(hydroxymethyl)pyrrolidin-1-yl | 597.44 |
| 23 | (R)-3-(hydroxymethyl)pyrrolidin-1-yl | 597.44 |
| 24 | 3-(hydroxymethyl)piperazin-1-yl racemic | 612.44 |
| 25 | (3R,4R)-4-amino-3-hydroxypiperidin-1-yl | 612.37 |

Example 26

(R)—N-(1-(7-Amino-4-(4-(morpholine-4-carbonyl)phenylamino)imidazo[1,2-f][1,2,4]triazin-2-yl)piperidin-3-yl)-4-tert-butylbenzamide

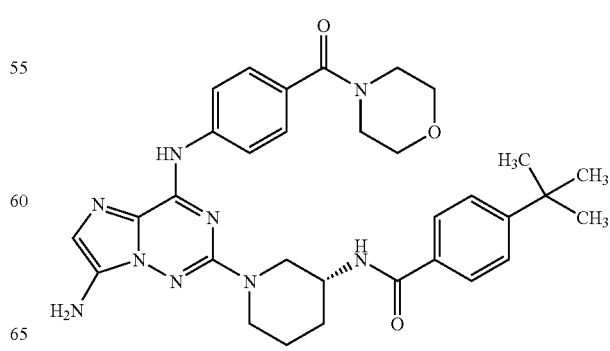

A. 7-Bromo-2,4-bis(methylthio)imidazo[1,2-f][1,2,4]triazine

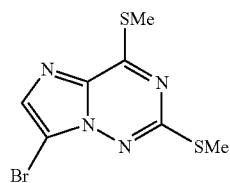

A mixture of 2,4-bis(methylthio)imidazo[1,2-f][1,2,4]triazine (3.0 g, 14.13 mmol) and NBS (3.52 g, 19.78 mmol) in CHCl$_3$ (60 mL) was heated at reflux for 1 hr. Upon cooling to rt, the mixture (heterogeneous) was diluted with ethyl acetate (250 mL), washed with 1 N Na$_2$CO$_3$ solution (3×50 mL) and brine (50 mL), and dried over anhydrous MgSO$_4$. The desired product, 7-bromo-2,4-bis(methylthio)imidazo[1,2-f][1,2,4]triazine (3.60 g, 12.36 mmol, 87% yield), was isolated as a white solid with ISCO chromatography (330 g silica gel, solid loading with 15 g silica gel, 100% CH$_2$Cl$_2$).

B. 2,4-Bis(methylthio)imidazo[1,2-f][1,2,4]triazine-7-carboxylic acid

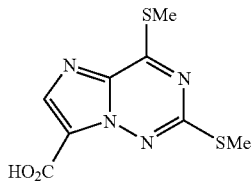

To a solution of 7-bromo-2,4-bis(methylthio)imidazo[1,2-f][1,2,4]triazine (0.500 g, 1.717 mmol) in THF (20 mL) at −78° C. was dropwise added n-butyllithium (0.756 mL, 1.889 mmol). The resulting yellow solution was stirred at −78° C. for 30 min before CO$_2$ (g) was bubbled through the solution over 5 min, during which period the solution turned cloudy. The mixture was stirred at −78° C. for 45 min and then allowed to warm to rt over 30 min. During this period a balloon was attached to the reaction flask through a needle to keep the flask from being over pressured. The reaction was quenched with water (50 mL). The resulting solution was neutralized with 1 N HCl to pH 5 and extracted with ethyl acetate (4×40 mL). The combined extract was washed with brine (50 mL) and dried over anhydrous MgSO$_4$. Evaporation of solvent under vacuum gave the desired product, 2,4-bis(methylthio)imidazo[1,2-f][1,2,4]triazine-7-carboxylic acid (0.359 g, 1.401 mmol, 82% yield), as a tan solid.

C. tert-Butyl 2,4-bis(methylthio)imidazo[1,2-f][1,2,4]triazin-7-ylcarbamate

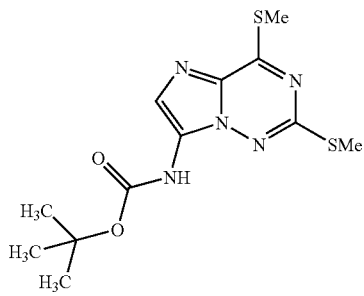

A mixture of 2,4-bis(methylthio)imidazo[1,2-f][1,2,4]triazine-7-carboxylic acid (0.350 g, 1.366 mmol), diphenyl phosphorazidate (0.324 mL, 1.502 mmol), N,N-diisopropylethylamine (0.262 mL, 1.502 mmol), and 2-methyl-2-propanol (10 mL, 105 mmol) was heated at reflux for 3 hr. The volatiles were removed under vacuum. The residue was diluted with ethyl acetate (80 mL), washed with 1 N NaHCO$_3$ solution (2×25 mL) and brine (25 mL), and dried over anhydrous MgSO$_4$. The desired product, tert-butyl 2,4-bis(methylthio)imidazo[1,2-f][1,2,4]triazin-7-ylcarbamate (0.359 g, 1.096 mmol, 80% yield), was isolated as a pale yellow solid with ISCO (40 g silica gel, 15-25% ethyl acetate/heptane).

D. tert-Butyl 2-(methylthio)-4-(4-(morpholine-4-carbonyl)phenylamino)imidazo[1,2-f][1,2,4]triazin-7-ylcarbamate

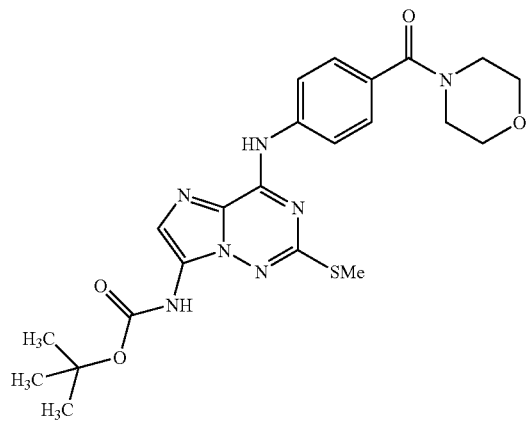

To a solution of (4-aminophenyl)(morpholino)methanone (0.231 g, 1.122 mmol) in THF (15 mL) at rt was added potassium t-butoxide (1.0 M in THF, 3.37 mL, 3.37 mmol) over 5 min, followed by the addition of tert-butyl 2,4-bis(methylthio)imidazo[1,2-f][1,2,4]triazin-7-ylcarbamate (0.350 g, 1.069 mmol) in THF (5 mL). The resulting dark red mixture was stirred at rt for 1 hr before the reaction was quenched with ice-cold water (50 mL). The mixture was adjusted with 1 N HCl to pH 9-10 and diluted with ethyl acetate (300 mL). The aqueous layer was separated, and the organic layer was washed with brine (50 mL) and dried over anhydrous MgSO$_4$. The solution was concentrated under vacuum to a volume of approximate 10 mL, and the precipitating product, tert-butyl 2-(methylthio)-4-(4-(morpholine-4-carbonyl)phenylamino)imidazo[1,2-f][1,2,4]triazin-7-ylcarbamate (0.387 g, 0.797 mmol, 74.6% yield), was collected as a pale yellow solid by suction filtration and dried under vacuum.

E. tert-butyl 2-(methylsulfonyl)-4-(4-(morpholine-4-carbonyl)phenylamino)imidazo[1,2-f][1,2,4]triazin-7-ylcarbamate

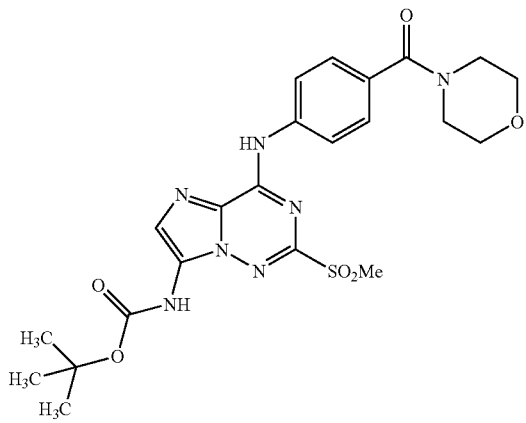

A mixture of tert-butyl 2-(methylthio)-4-(4-(morpholine-4-carbonyl)phenylamino)imidazo[1,2-f][1,2,4]triazin-7-yl-carbamate (0.380 g, 0.783 mmol) and mCPBA (0.438 g, 1.957 mmol) in THF (35 mL) was stirred at rt for 3 hr. It was concentrated under vacuum to a volume of approximate 15 mL. The residue was diluted with ethyl acetate (250 mL), washed sequentially with 5% $Na_2S_2O_3$ solution (2×50 mL), 1 N $Na_2CO_3$ solution (2×50 mL), and water (50 mL). During the washing product started to precipitate in organic phase. The organic layer was separated and concentrated under vacuum to a volume of approximate 10 mL. The precipitating product, tert-butyl 2-(methylsulfonyl)-4-(4-(morpholine-4carbonyl)phenylamino)imidazo[1,2-f][1,2,4]triazin-7-yl-carbamate (0.385 g, 0.744 mmol, 95% yield), was collected as a white solid by suction filtration and dried over $P_2O_5$ under vacuum.

F. (4-(7-amino-2-(methylsulfonyl)imidazo[1,2-f][1,2,4]triazin-4-ylamino)phenyl)(morpholino)methanone

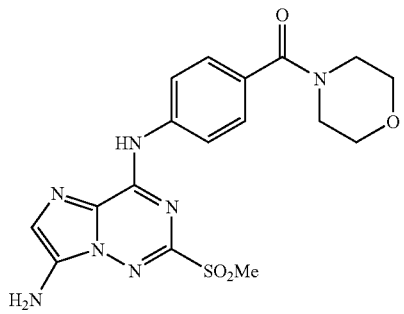

To a suspension of tert-butyl 2-(methylsulfonyl)-4-(4-(morpholine-4-carbonyl)phenylamino)imidazo[1,2-f][1,2,4]triazin-7-ylcarbamate (150 mg, 0.290 mmol) in $CH_2Cl_2$ (5 mL) at 0° C. was added TFA (5 mL, 64.9 mmol) over 2 min. The resulting solution was stirred at rt for 1 hr. The volatile was removed under vacuum. The residue was dissolved in ethyl acetate (80 mL), washed sequentially with 1 N $Na_2CO_3$ solution (2×25 mL) and brine (25 mL), and dried over anhydrous $MgSO_4$. Removal of solvent under vacuum provide the desired product, (4-(7-amino-2-(methylsulfonyl)imidazo[1,2-f][1,2,4]triazin-4-ylamino)phenyl)(morpholino)-methanone (120 mg, 0.287 mmol, 99% yield), as a yellow solid.

G. (R)—N-(1-(7-Amino-4-(4-(morpholine-4-carbonyl)phenylamino)imidazo[1,2-f][1,2,4]triazin-2-yl)piperidin-3-yl)-4-tert-butylbenzamide A mixture of (4-(7-amino-2-(methylsulfonyl)imidazo[1,2-f][1,2,4]triazin-4-ylamino)phenyl)(morpholino)methanone (120 mg, 0.287 mmol) and (R)-4-tert-butyl-N-(piperidin-3-yl)benzamide (187 mg, 0.719 mmol) was heated without any solvent at 160° C. for 7 hr. The mixture was dissolved in DMSO (1 mL), diluted with MeOH (5 mL), divided into five portions, and injected to prep. HPLC. The correct fractions were combined, concentrated under vacuum, basified with 1 N $NaHCO_3$ solution to pH 9. The precipitating product, (R)—N-(1-(7-amino-4-(4-(morpholine-4-carbonyl)phenylamino)imidazo[1,2-f][1,2,4]triazin-2-yl)piperidin-3-yl)-4-tert-butylbenzamide (27.5 mg, 0.046 mmol, 16.01% yield), was collected as a beige solid by suction filtration and dried over P2O5 under vacuum. LCMS (M+H)$^+$=598.41. $^1$H NMR (500 MHz, d6-DMSO) δ ppm 10.23 (s, 1H), 8.28 (d, J=8.25 Hz, 1H), 8.00 (d, J=8.80 Hz, 2H), 7.81 (d, J=8.25 Hz, 2H), 7.48 (d, J=8.25 Hz, 2H), 7.34 (d, J=8.80 Hz, 2 H), 6.74 (s, 1H), 5.25 (s, 2H), 4.51 (m, 1H), 4.34 (m, 1H), 3.98 (m, 1H), 3.60-3.40 (m, 8H), 2.95-2.85 (m, 2H), 1.95 (m, 1H), 1.83 (m, 1H), 1.67-1.60 (m, 2H), 1.30 (s, 9H).

Example 27

(R)—N-(1-(7-Amino-4-(4-(morpholine-4-carbonyl)phenylamino)imidazo[1,2-f][1,2,4]triazin-2-yl)piperidin-3-yl)benzamide

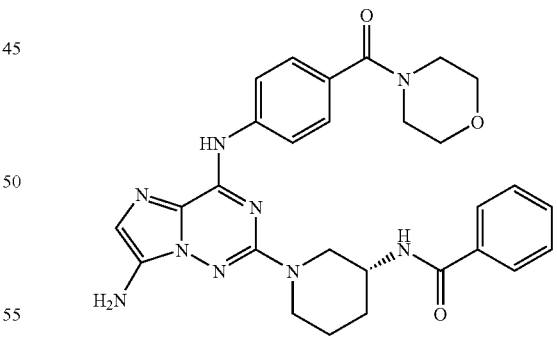

A mixture of (4-(7-amino-2-(methylsulfonyl)imidazo[1,2-f][1,2,4]triazin-4-ylamino)phenyl)(morpholino)methanone (100 mg, 0.240 mmol) and (R)—N-(piperidin-3-yl)benzamide (147 mg, 0.719 mmol) was heated without any solvent at 160° C. for 5 hr. At this point, the reaction was only 30% complete but otherwise it remained clean. On cooling to rt, the mixture was dissolved with DMSO (0.9 mL) and then diluted with MeOH (3.5 mL). The resulting solution was divided into four portions and injected to prep. HPLC. The correct fractions were combined, concentrated under vacuum, basified with 1 N NaHCO₃ solution to pH 9, and extracted with ethyl acetate (3×30 mL). The combined extract was washed with brine and dried over MgSO₄. Removal of solvent under vacuum provided the desired product, (R)—N-(1-(7-amino-4-(4-(morpholine-4-carbonyl)phenylamino)imidazo[1,2-f][1,2,4]triazin-2-yl)piperidin-3-yl)benzamide (10.4 mg, 0.019 mmol, 8.02% yield), as a beige solid. LCMS (M+H)⁺=542.21. ¹H NMR (500 MHz, d6-DMSO) δ ppm 10.22 (s, 1H), 8.35 (d, J=7.7 Hz, 1H), 8.00 (d, J=8.25 Hz, 2H), 7.87 (d, J=7.15 Hz, 2H), 7.53 (m, 1H), 7.46 (m, 2H), 7.35 (d, J=8.80 Hz, 2H), 6.74 (s, 1H), 5.24 (s, 2H), 4.52 (m, 1H), 4.33 (m, 1H), 3.98 m (m, 1H), 3.52-3.40 (m, 8H), 2.96-2.87 (m, 2H), 1.92 (m, 1H), 1.82 (m, 1H), 1.68-1.57 (m, 2H).

Example 28

(R)—N-(1-(7-Amino-4-(4-(morpholine-4-carbonyl)phenylamino)imidazo[1,2-f][1,2,4]triazin-2-yl)piperidin-3-yl)-1H-indole-2-carboxamide

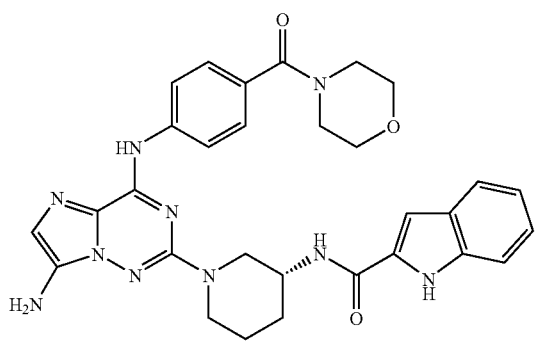

A mixture of (4-(7-amino-2-(methylsulfonyl)imidazo[1,2-f][1,2,4]triazin-4-ylamino)phenyl)(morpholino)methanone (80.0 mg, 0.192 mmol) and (R)—N-(piperidin-3-yl)-1H-indole-2-carboxamide (93 mg, 0.383 mmol) in N-Methyl-2-pyrrolidinone (0.5 mL) was heated at 160° C. for 20 hr. The mixture was diluted with MeOH (2 mL), divided into two portions, and injected to prep HPLC. The correct fractions were combined, concentrated under vacuum, basified with 1 N NaHCO₃ solution to pH 9, and extracted with ethyl acetate (3×25 mL). The combined extract was washed with brine and dried over MgSO₄. Removal of solvent under vacuum provided the desired product, (R)—N-(1-(7-amino-4-(4-(morpholine-4-carbonyl)phenylamino)imidazo[1,2-f][1,2,4]triazin-2-yl)piperidin-3-yl)-1H-indole-2-carboxamide (11.6 mg, 0.020 mmol, 10.42% yield), as a beige solid. LCMS (M+H)⁺=581.22. ¹H NMR (500 MHz, d6-DMSO) δ ppm 11.6 (s, 1H), 10.3 (s, 1H), 8.35 (d, J=7.7 Hz, 1H), 7.97 (d, J=8.25 Hz, 2H), 7.60 (d, J=7.7 Hz, 1H), 7.44 (d, J=8.25 Hz, 1H), 7.36 (d, J=8.25 Hz, 2H), 7.19-7.16 (m, 2H), 7.03 (m, 1H), 6.82 (br. s, 1H), 5.40 (br. s, 2H), 4.52 (m, 1H), 4.36 (m, 1H), 4.03 (m, 1H), 3.60-3.30 (m, 8H), 3.00-2.90 (m, 2H), 1.99 (m, 1H), 1.85 (m, 1H), 1.68-1.60 (m, 2H).

Example 29

(R)—N-(1-(7-acetamido-4-(4-(morpholine-4-carbonyl)phenylamino)imidazo[1,2-f][1,2,4]triazin-2-yl)piperidin-3-yl)-1H-indole-2-carboxamide

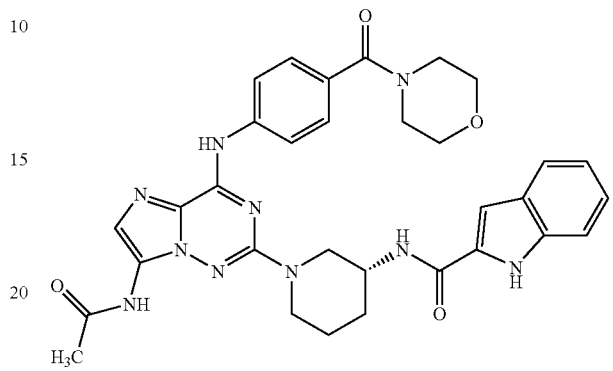

A mixture of (R)—N-(1-(7-amino-4-(4-(morpholine-4-carbonyl)phenylamino)imidazo[1,2-f][1,2,4]triazin-2-yl)piperidin-3-yl)-1H-indole-2-carboxamide (30 mg, 0.052 mmol), acetic acid (4.65 mg, 0.078 mmol), BOP (41.1 mg, 0.093 mmol), and 4-Methylmorpholine (0.031 mL, 0.279 mmol) in DMF (1.5 mL) was heated at 60° C. for 20 hr. The solution was diluted with ethyl acetate (60 mL), washed with water (2×20 mL) and brine, and dried over anhydrous MgSO₄. The solvent was removed under vacuum, and the residue was injected to prep. HPLC. The correct fraction was concentrated under vacuum, basified with 1 N Na₂CO₃ solution. The precipitating product, (R)—N-(1-(7-acetamido-4-(4-(morpholine-4-carbonyl)phenylamino)imidazo[1,2-f][1,2,4]triazin-2-yl)piperidin-3-yl)-1H-indole-2-carboxamide (1.93 mg, 3.10 mmol, 6% yield) was collected as a pale yellow solid by suction filtration and dried over P₂O₅. LCMS (M+H)⁺=623.40.

Example 30

(R)-2-(3-Benzamidopiperidin-1-yl)-4-(4-(morpholine-4-carbonyl)phenylamino)imidazo[1,2-f][1,2,4]-triazine-7-carboxamide

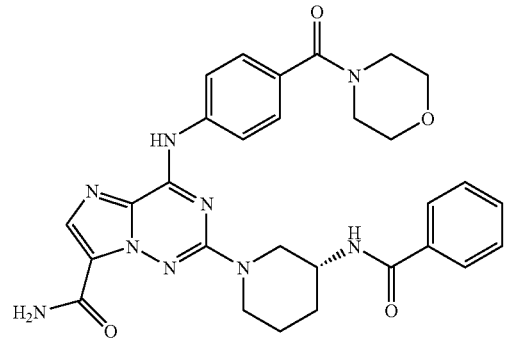

A. 2,4-Bis(methylthio)imidazo[1,2-f][1,2,4]-triazine-7-carboxamide

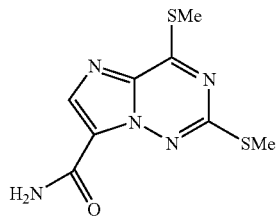

To 2,4-bis(methylthio)imidazo[1,2-f][1,2,4]triazine-7-carboxylic acid (0.375 g, 1.463 mmol) was added refrigerated cold thionyl chloride (10 mL, 137 mmol). The heterogeneous mixture was stirred at rt for 2 hr. No reaction occurred. Thus, the mixture was heated at reflux for 30 min, and then the volatiles were removed under vacuum. To the solid residue was added ammonium hydroxide (25 mL, 193 mmol), and the resulting heterogeneous mixture was stirred at rt for 30 min. The insoluble product, 2,4-bis(methylthio)imidazo[1,2-f][1,2,4]triazine-7-carboxamide (0.322 g, 1.261 mmol, 86% yield), was collected by suction filtration and dried over drierite under vacuum.

B. 2-(Methylthio)-4-(4-(morpholine-4-carbonyl)phenylamino)imidazo[1,2-f][1,2,4]triazine-7-carboxamide

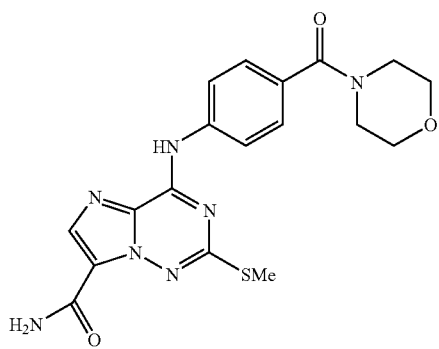

To a solution of 2,4-bis(methylthio)imidazo[1,2-f][1,2,4]triazine-7-carboxamide (0.320 g, 1.25 mmol) in THF (20 mL) at rt was added potassium tert-butoxide solution (4.37 mL, 4.37 mmol) over 5 min, followed by the addition of 2,4-bis(methylthio)imidazo[1,2-f][1,2,4]triazine-7-carboxamide (0.272 g, 1.32 mmol) in THF (60 mL). The resulting mixture was stirred at rt for 1 hr before it was poured into ice-cold water (100 mL). The mixture was adjusted with 1 N HCl to pH 9-10 and extracted with ethyl acetate (3×80 mL). The combined extract was washed with brine (80 mL), dried over anhydrous MgSO$_4$, and concentrated under vacuum. The residue was triturated with methanol (10 mL) to provide the desired product (291 mg, 56% yield).

C. 2-(Methylsulfonyl)-4-(4-(morpholine-4-carbonyl)phenylamino)imidazo[1,2-f][1,2,4]triazine-7-carboxamide

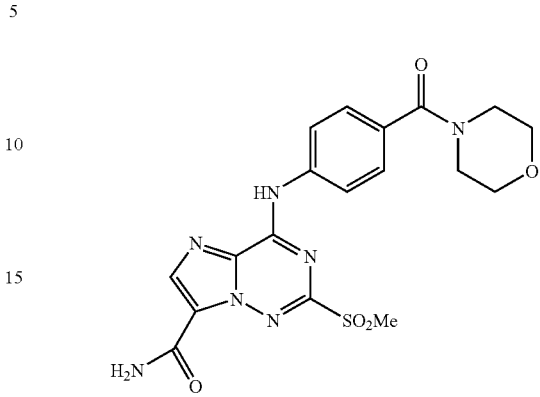

A mixture of 2-(methylthio)-4-(4-(morpholine-4-carbonyl)phenylamino)imidazo[1,2-f][1,2,4]triazine-7-carboxamide (185 mg, 0.447 mmol) and mCPBA (341 mg, 1.521 mmol) in THF (20 mL) was stirred at rt for 6 hr. It was concentrated under vacuum to a volume of approximate 5 mL. The residue was diluted with ethyl acetate (150 mL), washed sequentially with 5% Na$_2$S$_2$O$_3$ solution (2×35 mL), 1 N Na$_2$CO$_3$ solution (2×35 mL), and water (40 mL). During the washing product started to precipitate in organic phase. The organic layer was separated, and the aqueous layer was extracted with ethyl acetate (100 mL). The combined organic phase was concentrated to dryness under vacuum. To the residue was added water (5 mL), and the insoluble product, 2-(methylsulfonyl)-4-(4-(morpholine-4-carbonyl)phenylamino)imidazo[1,2-f][1,2,4]triazine-7-carboxamide (84 mg, 0.189 mmol, 42.1% yield), was collected by suction filtration and dried over drierite under vacuum.

D. (R)-2-(3-Benzamidopiperidin-1-yl)-4-(4-(morpholine-4-carbonyl)phenylamino)imidazo[1,2-f][1,2,4]triazine-7-carboxamide A mixture of 2-(methylsulfonyl)-4-(4-(morpholine-4-carbonyl)phenylamino)imidazo[1,2-f][1,2,4]triazine-7-carboxamide (40 mg, 0.090 mmol) and (R)—N-(piperidin-3-yl)benzamide (45.9 mg, 0.224 mmol) in N-methyl-2-pyrrolidinone (0.4 mL) was heated at 150° C. for 16 hr. On cooling to rt, the mixture was diluted with MeOH (2 mL), divided into two portions, and injected to prep. HPLC. The correct fractions were combined, concentrated under vacuum, basified to pH 9 with saturated Na$_2$CO$_3$ solution, and extracted with ethyl acetate (3×40 mL). During the extraction, the product was transferred into the organic layer, but it was not completely dissolved. The combined organic phase was concentrated under vacuum to a volume of approximately 5 mL. To this residue was added water (1 mL). The insoluble product, (R)-2-(3-benzamidopiperidin-1-yl)-4-(4-(morpholine-4-carbonyl)phenylamino)imidazo[1,2-f][1,2,4]triazine-7-carboxamide (15.7 mg, 0.028 mmol, 30.7% yield), was collected by suction filtration and dried over P$_2$O$_5$ under vacuum. LCMS (M+H)$^+$=570.33; $^1$H NMR (400 MHz, d6-DMSO) δ ppm 10.8 (s, 1H), 8.40 (d, J=7.3 Hz, 1H), 8.17 (s, 1H), 8.03 (d, J=8.6 Hz, 2H), 7.97 (s, 1H), 7.94 (s, 1H), 7.89 (m, 2H), 7.54 (m, 1H), 7.81 (d, J=7.8 Hz, 2H), 7.43 (d, J=8.6

Hz, 2H), 4.47 (m, 1H), 4.18 (m, 1H), 4.01 (m, 1H), 3.62-3.44 (m, 8H), 3.15-3.01 (m, 2H), 1.99 (m, 1H), 1.88 (m, 1H), 1.78-1.61 (m, 2H).

Example 31

(R)-2-(3-(1H-indole-2-carboxamido)piperidin-1-yl)-4-(4-(morpholine-4-carbonyl)phenylamino)imidazo[1,2-f][1,2,4]-triazine-7-carboxamide

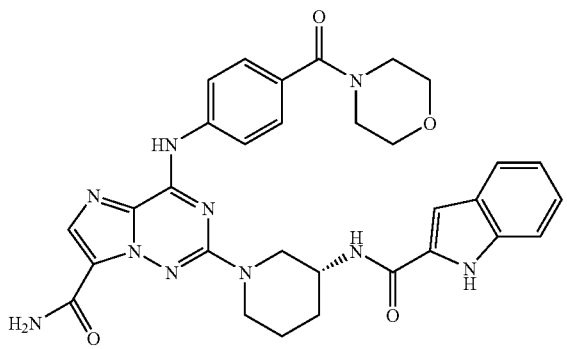

This compound was synthesized in the same manner as example 28 was. LCMS (M+H)$^+$=609.38; $^1$H NMR (500 MHz, d6-DMSO) δ ppm 11.6 (s, 1H), 10.8 (s, 1H), 8.42 (d, J=7.7 Hz, 1H), 8.25 (s, 1H), 7.99 (d, J=8.3 Hz, 2H), 7.96 (s, 1H), 7.86 (s, 1H), 7.60 (d, J=7.7 Hz, 1H), 7.44-7.40 (m, 3H), 7.20-7.17 (m, 2H), 7.03 (m, 1H), 4.46 (m, 1H), 4.22 (m, 1H), 4.03 (m, 1H), 3.58-3.41 (m, 8H), 3.09 (m, 1H), 2.98 (m, 1H), 1.87 (m, 1H), 1.85 (m, 1H), 1.73-1.62 (m, 2H).

Example 32

(R)-4-tert-Butyl-N-(1-(7-cyano-4-(4-(morpholine-4-carbonyl)phenylamino)imidazo[1,2-f][1,2,4]triazin-2-yl)piperidin-3-yl)benzamide

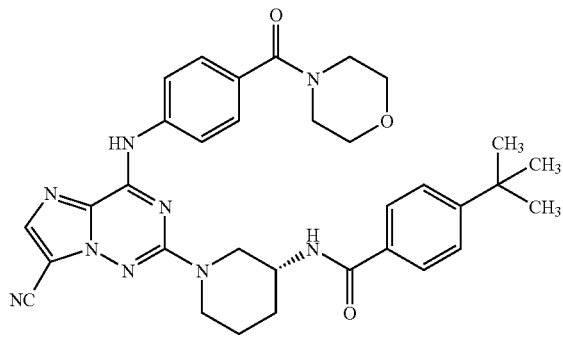

A. 2,4-Bis(methylthio)imidazo[1,2-f][1,2,4]triazine-7-carbonitrile

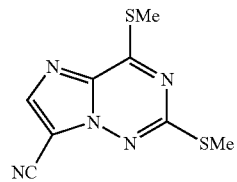

A solution of 7-bromo-2,4-bis(methylthio)imidazo[1,2-f][1,2,4]triazine (0.5023 g, 1.725 mmol), zinc (0.011 g, 0.172 mmol), DPPF (0.038 g, 0.069 mmol), Pd$_2$dba$_3$ (0.032 g, 0.034 mmol) and zinc cyanide (0.122 g, 1.035 mmol) in DMA (4.31 mL) was purged with nitrogen, sealed and microwaved at 150° C. for 15 min and cooled to room temperature. This reaction was repeated which was then combined, diluted with EtOAc and washed with 10% aq. LiCl (2×) and brine, successively, dried over Na$_2$SO$_4$, filtered and concentrated in vacuo. This was triturated with CH$_2$Cl$_2$ to give 2,4-bis(methylthio)imidazo[1,2-f][1,2,4]triazine-7-carbonitrile (351.6 mg tan solid, 21.5% yield).

B. 2-(Methylthio)-4-(4-(morpholine-4-carbonyl)phenylamino)imidazo[1,2-f][1,2,4]triazine-7-carbonitrile To a solution of (4-aminophenyl)(morpholino)methanone (0.545 g, 2.64 mmol) in THF (45 mL) at rt was added potassium tert-butoxide solution (5.28 mL, 5.28 mmol) over 5 min, followed by the addition of 2,4-bis(methylthio)imidazo[1,2-f][1,2,4]triazine-7-carbonitrile (0.597 g, 2.52 mmol) in THF (35 mL). The resulting mixture was stirred at rt for 1 hr before it was poured into ice-cold water (150 mL). The mixture was adjusted with 1 N HCl to pH 9-10 and extracted with ethyl acetate (3×80 mL). The combined extract was washed with brine (80 mL) and dried over anhydrous MgSO$_4$. The desired product, 2-(methylthio)-4-(4-(morpholine-4-carbonyl)phenylamino)imidazo[1,2-f][1,2,4]triazine-7-carbonitrile (0.831 g, 2.101 mmol, 84% yield), was isolated as a yellow solid with ISCO chromatography (80 g silica gel, 70-100 ethyl acetate/heptane).

C. 2-(Methylsulfonyl)-4-(4-(morpholine-4-carbonyl)phenylamino)imidazo[1,2-f][1,2,4]triazine-7-carbonitrile

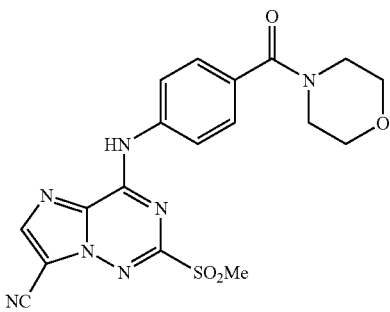

A mixture of 2-(methylthio)-4-(4-(morpholine-4-carbonyl)phenylamino)imidazo[1,2-f][1,2,4]triazine-7-carbonitrile (0.831 g, 2.101 mmol) and mCPBA (1.177 g, 5.25 mmol) in THF (50 mL) was stirred at rt for 3 hr. It was concentrated under vacuum to a volume of approximate 20 mL. The residue was diluted with ethyl acetate (150 mL), washed sequentially with 5% $Na_2S_2O_3$ solution (2×50 mL), 1 N $Na_2CO_3$ solution (2×50 mL), and brine (50 mL). The solution was dried over anhydrous $MgSO_4$. Removal of the solvent under vacuum provided the desired product (1.08 g) as a white solid. This product was a 1:1 eq. ethyl acetate solvate.

D. (R)-4-tert-Butyl-N-(1-(7-cyano-4-(4-(morpholine-4-carbonyl)phenylamino)imidazo[1,2-f][1,2,4]triazin-2-yl)piperidin-3-yl)benzamide A mixture of 2-(methylsulfonyl)-4-(4-(morpholine-4-carbonyl)phenylamino)imidazo[1,2-f][1,2,4]triazine-7-carbonitrile (82% purity) (250 mg, 0.480 mmol) and (R)-4-tert-butyl-N-(piperidin-3-yl)benzamide (335 mg, 1.287 mmol) in N-Methyl-2-pyrrolidinone (2 mL) was heated at 150° C. for 16 hr. The mixture was diluted with ethyl acetate (100 mL), washed sequentially with water (3×25 mL) and brine (25 mL), and dried over anhydrous $MgSO_4$. The desired product (167 mg) was isolated by ISCO chromatography (40 g silica gel, solid loading, 80-100% ethyl acetate/heptane). $^1H$ NMR (500 MHz, d6-DMSO) δ ppm 11.0 (s, 1H), 8.31 (d, J=7.7 Hz, 1H), 8.26 (s, 1H), 8.01 (d, J=8.8 Hz, 2H), 7.81 (d, J=8.3 Hz, 2H), 7.48 (d, J=8.8 Hz, 2H), 7.41 (d, J=8.3 Hz, 2H), 4.50 (m, 1H), 4.24 (m, 1H), 3.99 (m, 1H), 3.61-3.40 (m, 8H), 3.08-2.97 (m, 2H), 1.97 (m, 1H), 1.89 (m, 1H), 1.73-1.61 (m, 2H), 1.31 (s, 9H).

Example 33

(R)—N-(1-(7-Cyano-4-(4-(morpholine-4-carbonyl)phenylamino)imidazo[1,2-f][1,2,4]triazin-2-yl)piperidin-3-yl)-1H-indole-2-carboxamide

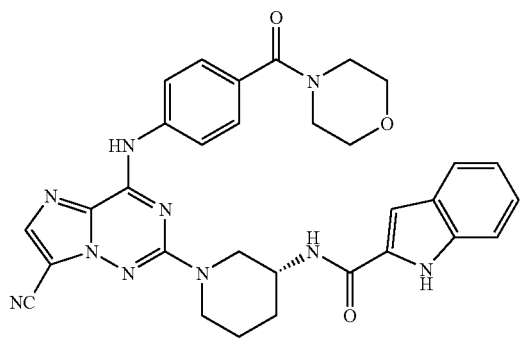

This compound was prepared using the same procedure for the preparation of Example 30. LCMS $(M+H)^+$=591.31; $^1H$ NMR (500 MHz, d6-DMSO) δ ppm 11.6 (s, 1H), 11.0 (s, 1H), 8.39 (d, J=7.7 Hz, 1H), 8.27 (s, 1H), 7.99 (d, J=8.3 Hz, 2H), 7.61 (d, J=7.7 Hz, 1H), 7.46-7.41 (m, 4H), 7.20-7.17 (m, 2H), 7.04 (m, 1H), 4.50 (m, 1H), 4.27 (m, 1H), 4.03 (m, 1H), 3.57-3.41 (m, 8H), 3.09-2.98 (m, 2H), 2.01 (m, 1H), 1.89 (m, 1H), 1.72-1.60 (m, 2H), 1.31 (s, 9H).

Example 34

(R)—N-(1-(7-(Aminomethyl)-4-(4-(morpholine-4-carbonyl)phenylamino)imidazo[1,2-f][1,2,4]triazin-2-yl)piperidin-3-yl)-4-tert-butylbenzamide

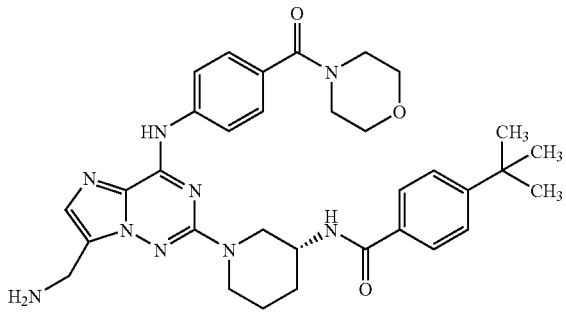

(R)-4-tert-butyl-N-(1-(7-cyano-4-(4-(morpholine-4-carbonyl)phenylamino)imidazo[1,2-f][1,2,4]triazin-2-yl)piperidin-3-yl)benzamide (113 mg, 0.186 mmol) was dissolved in THF (1 mL) and then diluted with ammonia (7 M in MeOH) (10 mL, 70.0 mmol). To this solution was added a small spatula of Raney Ni (50% water slurry), and the mixture was stirred at rt under $H_2$, provided with a $H_2$ balloon, for 1.5 hr. The catalyst was removed by suction filtration. The filtrate was diluted with ethyl acetate (80 mL), washed sequentially with water (20 mL) and brine (20 mL), and dried over anhydrous $MgSO_4$. The product was isolated by prep. HPLC. The correct fractions were combined, concentrated under vacuum, basified with 1 N $NaHCO_3$ solution, and extracted with ethyl acetate (3×25 mL). The combined extract was dried over $MgSO_4$. Removal of the solvent under vacuum provided the desired product, (R)—N-(1-(7-(aminomethyl)-4-(4-(morpholine-4-carbonyl)phenylamino)imidazo[1,2-f][1,2,4]triazin-2-yl)piperidin-3-yl)-4-tert-butylbenzamide (10.1 mg, 0.017 mmol, 8.88% yield), as a white solid. LCMS $(M+H)^+$=612.43; $^1H$ NMR (500 MHz, d6-DMSO) δ ppm 11.5 (s, 1H), 8.26 (d, J=7.2 Hz, 1H), 8.02 (d, J=7.7 Hz, 2H), 7.80 (d, J=7.7 Hz, 2H), 7.46 (d, J=7.7 Hz, 2H), 7.38 (s, 1H), 7.37 (d, J=8.3 Hz, 2H), 4.50 (m, 1H), 4.24 (m, 1H), 3.97 (m, 1H), 3.89 (s, 2H), 3.60-3.42 (m, 8H), 3.00-2.89 (m, 2H), 1.93 (m, 1H), 1.82 (m, 1H), 1.71-1.58 (m, 2H), 1.29 (s, 9H).

Example 35

(R)—N-(1-(7-(Aminomethyl)-4-(4-(morpholine-4-carbonyl)phenylamino)imidazo[1,2-f][1,2,4]triazin-2-yl)piperidin-3-yl)-1H-indole-2-carboxamide

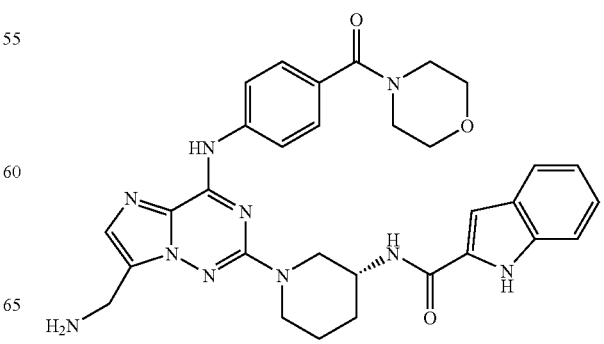

This compound was prepared in the same manner as Example 32 was. LCMS (M+H)⁺=595.37; $^1$H NMR (500 MHz, d6-DMSO) δ ppm 11.6 (s, 1H), 8.36 (d, J=7.7 Hz, 1H), 8.00 (d, J=8.8 Hz, 2H), 7.80 (d, J=7.7 Hz, 2H), 7.60 (d, J=8.3 Hz, 2H), 7.43 (d, J=8.3 Hz, 1H), 7.39-7.37 (m, 4H), 7.19-7.16 (m, 2H), 7.03 (m, 1H), 4.50 (m, 1H), 4.24 (m, 1H), 4.02 (m, 1H), 3.90 (s, 2H), 3.58-3.40 (m, 8H), 3.01-2.90 (m, 2H), 1.99 (m, 1H), 1.86 (m, 1H), 1.69-1.60 (m, 2H).

Example 36

(R)—N-(1-(4-(4-(morpholine-4-carbonyl)phenylamino)imidazo[1,2-f][1,2,4]triazin-2-yl)piperidin-3-yl)benzamide

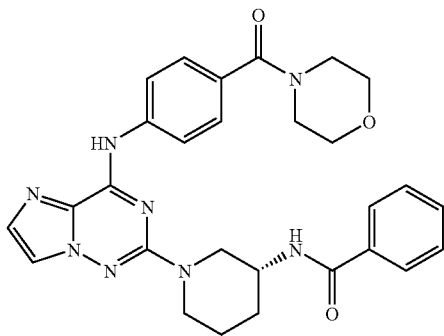

This compound was synthesized in the same manner as (R)-4-tert-Butyl-N-(1-(4-(4-(morpholine-4-carbonyl)phenylamino)imidazo[1,2-f][1,2,4]triazin-2-yl)piperidin-3-yl) benzamide (Example 1) was synthesized. Beige solid; LCMS (M+H)⁺=527.18.

We claim:

1. A compound according to formula (I):

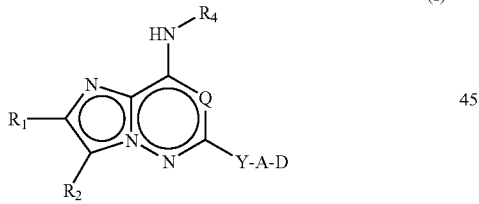

or an enantiomer, diastereomer, or a pharmaceutically-acceptable salt thereof, wherein Q is N;

Y is $NR_6R_7$, wherein $R_6$ and $R_7$ are taken together with the nitrogen atom to which they are both attached to form an optionally substituted heterocyclo or optionally substituted heteroaryl;

A is selected from $NH_2$ and $NHCONH_2$ provided D is absent;

A is selected from NH, NHCO, and NHCONH, provided D is other than absent;

A is selected from NHCOO, provided D is other than optionally substituted alkoxy or absent;

D is optionally substituted alkyl, optionally substituted alkoxy, optionally substituted cycloalkyl, optionally substituted aryl, optionally substituted heterocyclo, optionally substituted heteroaryl or is absent;

$R_1$ is selected from hydrogen, optionally substituted $C_{1-4}$ alkyl, and cyano;

$R_2$ is selected from hydrogen, optionally substituted $C_{1-4}$ alkyl, amino, cyano, optionally substituted amide, and optionally substituted carboxamide; and $R_4$ is selected from hydrogen, optionally substituted aryl, optionally substituted heterocyclo and optionally substituted heteroaryl.

2. A compound according to formula (II):

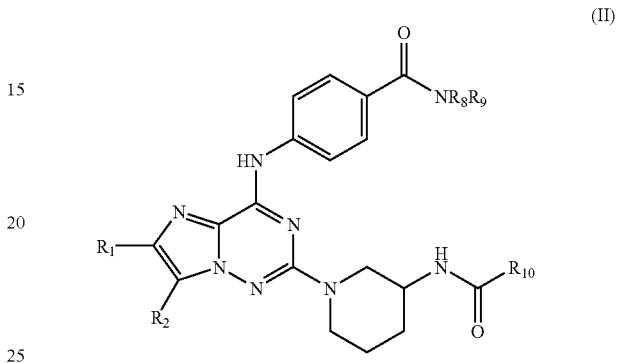

or an enantiomer, diastereomer, or a pharmaceutically-acceptable salt thereof, wherein $R_1$ is hydrogen;

$R_2$ is selected from hydrogen, amino, cyano, $C_{1-4}$ alkyl optionally substituted with amino, —C(═O)$NR_{11}R_{12}$, and —$NR_{11}$C(═O)$R_{12}$, wherein $R_{11}$ and $R_{12}$ are each independently selected from hydrogen, $C_{1-4}$ alkyl, $C_{3-7}$cycloalkyl, aryl, heteroaryl, and heterocyclo;

$R_8$ and $R_9$ are each independently selected from hydrogen, optionally substituted alkyl, optionally substituted alkoxy, optionally substituted cycloalkyl, and optionally substituted heterocyclo; or $R_8$ and $R_9$ may be taken together with the nitrogen atom to which they are both attached to form an optionally substituted heterocyclo or optionally substituted heteroaryl; and $R_{10}$ is selected from optionally substituted alkyl, optionally substituted alkoxy, optionally substituted cycloalkyl, optionally substituted aryl, optionally substituted heterocyclo and optionally substituted heteroaryl.

3. The compound according to claim 2, wherein $R_8$ and $R_9$ are each independently selected from hydrogen, $C_{1-4}$alkyl, heteroaryl and heterocyclo, wherein said $C_{1-4}$alkyl, heteroaryl and heterocyclo are optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —$NR_{13}R_{14}$, and —C(O)$OR_{13}$ wherein $R_{13}$ and $R_{14}$ are each independently selected from hydrogen, $C_{1-4}$alkyl, and heterocyclo.

4. The compound according to claim 3, wherein —$NR_8R_9$ is selected from

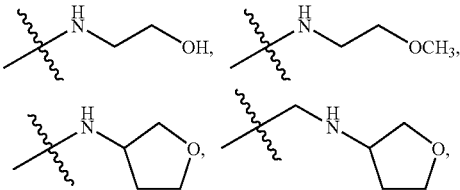

-continued

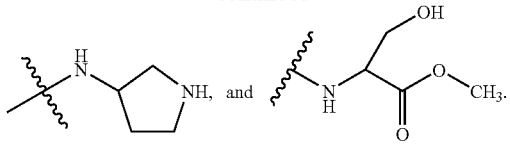

5. The compound according to claim 2, wherein $R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, wherein said heteroaryl and heterocyclo are independently optionally substituted as valence allows with one or more substituents selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —O($C_{1-4}$ alkyl), —C(=O)H, —C(=O), —S($C_{1-4}$ alkyl), —NH$_2$, —NH($C_{1-4}$alkyl), —N($C_{1-4}$alkyl)$_2$, and —NH(alkylene)OR$_{17}$ wherein $R_{17}$ is selected from hydrogen and $C_{1-4}$alkyl.

6. The compound according to claim 5, wherein —NR$_8$R$_9$ is selected from

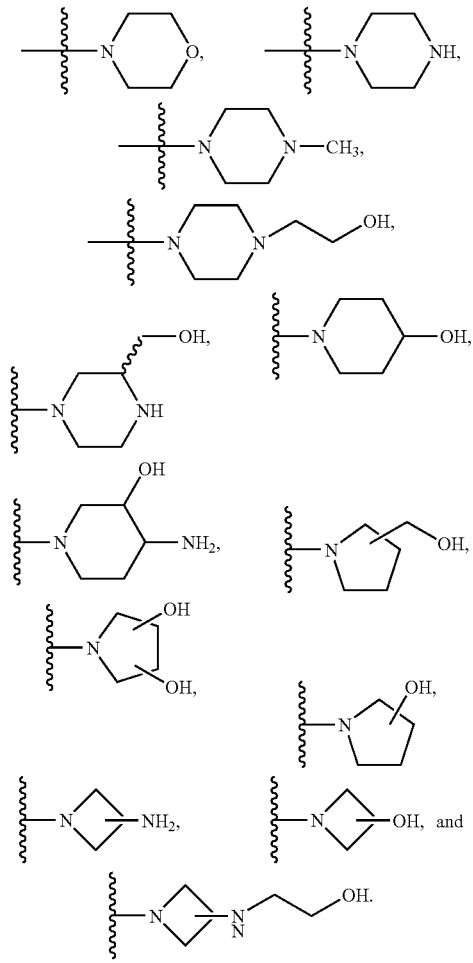

7. The compound according to claim 2, wherein $R_{10}$ is selected from aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —OR$_{15}$, —NR$_{15}$R$_{16}$, —NR$_{15}$C(=O)R$_{16}$, —CO$_2$R$_{15}$, —C(=O)R$_{15}$, —O—C(=O)R$_{15}$, —C(=O)NR$_{15}$R$_{16}$, cycloalkyl, heterocyclo, aryl, and heteroaryl wherein said cycloalkyl, aryl, heterocyclo, and heteroaryl are independently optionally substituted as valence allows with one or more $R_{18}$;

$R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo.

8. The compound according to claim 7, wherein $R_{10}$ is selected from

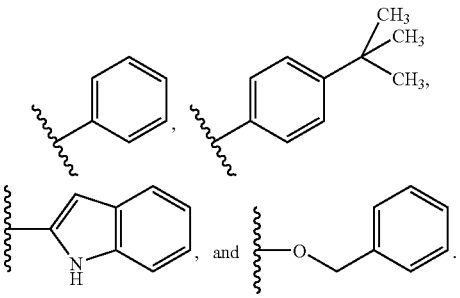

9. The compound according to claim 2, wherein
$R_1$ is hydrogen;
$R_2$ is selected from hydrogen, amino, cyano, $C_{1-4}$ alkyl optionally substituted with amino, —C(=O)NR$_{11}$R$_{12}$, and —NR$_{11}$C(=O)R$_{12}$, wherein $R_{11}$ and $R_{12}$ are each independently selected from hydrogen, $C_{1-4}$alkyl, $C_{3-7}$cycloalkyl, aryl, heteroaryl, and heterocyclo;
$R_8$ and $R_9$ are each independently selected from hydrogen, $C_{1-4}$alkyl, heteroaryl and heterocyclo, wherein said $C_{1-4}$alkyl, heteroaryl and heterocyclo are optionally substituted with one or more substituents selected from halogen, cyano, hydroxy, $C_{1-4}$alkoxy, $C_{1-4}$alkyl, haloalkyl, $C_{3-7}$cycloalkyl, heterocyclo, —NR$_{13}$R$_{14}$, and —C(O)OR$_{13}$ wherein $R_{13}$ and $R_{14}$ are each independently selected from hydrogen, $C_{1-4}$alkyl, and heterocyclo; or
$R_8$ and $R_9$ are taken together with the nitrogen atom to which they are both attached to form a 5- to 7-membered monocyclic heteroaryl or heterocyclo, or a 7- to 11-membered bicyclic heteroaryl or heterocyclo, wherein said heteroaryl and heterocyclo are independently optionally substituted as valence allows with one or more substituents selected from hydrogen, optionally substituted $C_{1-4}$alkyl, optionally substituted $C_{2-4}$alkenyl, optionally substituted $C_{2-4}$alkynyl, halogen, hydroxy, haloalkyl, hydroxyalkyl, cyano, nitro, —O($C_{1-4}$alkyl), —C(=O)H, —C(=O), —S($C_{1-4}$ alkyl), —NH$_2$, —NH($C_{1-4}$alkyl), —N($C_{1-4}$alkyl)$_2$, —NH(alkylene)OR$_{17}$ wherein $R_{17}$ is selected from hydrogen and $C_{1-4}$alkyl;
$R_{10}$ is selected from alkoxy, aryl, 5- to 7-membered monocyclic heteroaryl or heterocyclo, and 7- to 11-membered bicyclic heteroaryl or heterocyclo, any of which may be independently optionally substituted as valence allows with one or more substituents selected from halogen, alkyl, substituted alkyl, alkenyl, substituted alkenyl, alkynyl, substituted alkynyl, nitro, cyano, —$OR_{15}$, —$NR_{15}R_{16}$, —$NR_{15}C(=O)R_{16}$, —$CO_2R_{15}$, —$C(=O)R_{15}$, —O—$C(=O)R_{15}$, —$C(=O)NR_{15}R_{16}$, cycloalkyl, heterocyclo, aryl, and heteroaryl wherein said cycloalkyl, aryl, heterocyclo, and heteroaryl are independently optionally substituted as valence allows with one or more $R_{18}$;

$R_{15}$ and $R_{16}$ are each independently selected from hydrogen, alkyl, substituted alkyl, alkenyl, substituted alkenyl, cycloalkyl, aryl, heteroaryl, and heterocyclo; and $R_{18}$ is selected from hydrogen, halogen, hydroxyl, alkoxy, alkyl, substituted alkyl, alkenyl, substituted alkenyl, cycloalkyl, aryl, heteroaryl, and heterocyclo.

10. A pharmaceutical composition comprising one or more compounds according to claim 1 and a pharmaceutically acceptable carrier or diluent.

11. A method of treating rheumatoid arthritis comprising administering to a patient in need of such treatment a therapeutically-effective amount of a compound according to claim 2.

* * * * *

UNITED STATES PATENT AND TRADEMARK OFFICE
CERTIFICATE OF CORRECTION

PATENT NO. : 8,188,272 B2  
APPLICATION NO. : 12/532330  
DATED : May 29, 2012  
INVENTOR(S) : Chunjian Liu et al.

It is certified that error appears in the above-identified patent and that said Letters Patent is hereby corrected as shown below:

In the Abstract:

First Page, Col. 1 (Abstract), line 3

Delete "[PLEASE INSERT CHEMICAL STRUCTURE HERE] (I)" and insert -- 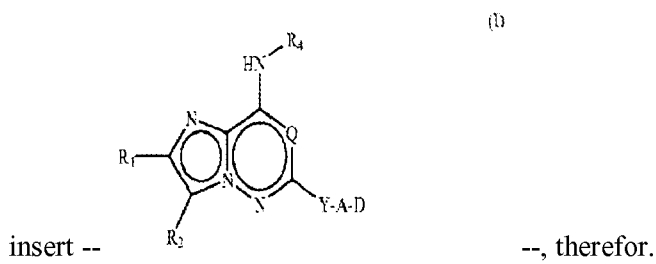 --, therefor.

First Page, Col. 1 (Abstract), line 6 (structure)

Below "are as defined herein."

delete " 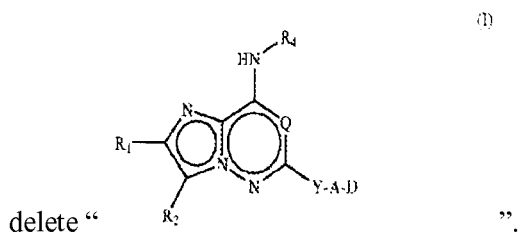 ".

Signed and Sealed this  
Twenty-ninth Day of January, 2013

David J. Kappos  
*Director of the United States Patent and Trademark Office*